United States Patent
Fang et al.

(10) Patent No.: US 12,171,840 B2
(45) Date of Patent: Dec. 24, 2024

(54) ANTI-MESOTHELIN ANTIBODY AND ANTIBODY DRUG CONJUGATE THEREOF

(71) Applicant: Remegen, Ltd., Yantai (CN)

(72) Inventors: Jianmin Fang, Yantai (CN); Changjiang Huang, Yantai (CN); Jing Jiang, Yantai (CN); Hui Ye, Yantai (CN); Shenjun Li, Yantai (CN); Qiaoyu Xu, Yantai (CN); Wenting Luo, Yantai (CN); Mingxue Wang, Yantai (CN)

(73) Assignee: RemeGen, Ltd., Yantai (CN)

( * ) Notice: Subject to any disclaimer, the term of this patent is extended or adjusted under 35 U.S.C. 154(b) by 1001 days.

(21) Appl. No.: 16/644,842

(22) PCT Filed: May 15, 2019

(86) PCT No.: PCT/CN2019/086977
§ 371 (c)(1),
(2) Date: Aug. 26, 2021

(87) PCT Pub. No.: WO2019/223579
PCT Pub. Date: Nov. 28, 2019

(65) Prior Publication Data
US 2022/0056147 A1 Feb. 24, 2022

(30) Foreign Application Priority Data
May 21, 2018 (CN) .......................... 201810487856.4

(51) Int. Cl.
C07K 16/30 (2006.01)
A61K 38/07 (2006.01)
(Continued)

(52) U.S. Cl.
CPC .......... *A61K 47/6889* (2017.08); *A61K 38/07* (2013.01); *A61K 47/65* (2017.08);
(Continued)

(58) Field of Classification Search
None
See application file for complete search history.

(56) References Cited

U.S. PATENT DOCUMENTS

2012/0189644 A1 7/2012 Kahnert et al.
2012/0225013 A1 9/2012 Dennis et al.
(Continued)

FOREIGN PATENT DOCUMENTS

CN 102458477 A 5/2012
CN 104470544 A 3/2015
(Continued)

OTHER PUBLICATIONS

Jain et al., Pharm Res (2015) 32:3526-3540 (Year: 2015).*
(Continued)

*Primary Examiner* — Karl J Puttlitz
(74) *Attorney, Agent, or Firm* — Wolf, Greenfield & Sacks, P.C.

(57) ABSTRACT

The present invention discloses an antibody drug conjugate that targets MSLN. The present invention also disclosed a method of making the antibody drug conjugate (ADC). The present invention further discloses a novel MSLN antibody or a functional fragment thereof comprising engineered heavy and light chains.

20 Claims, 8 Drawing Sheets

Specification includes a Sequence Listing.

1. RC88 antibody
2. RC88-PY-MAA-Val-Cit-PAB-MMAE
3. RC88-Mc-Val-Cit-PAB-MMAE

(51) Int. Cl.
  *A61K 47/65* (2017.01)
  *A61K 47/68* (2017.01)
  *A61P 35/00* (2006.01)
  *A61K 39/00* (2006.01)
(52) U.S. Cl.
  CPC .... *A61K 47/68031* (2023.08); *A61K 47/6811* (2017.08); *A61K 47/6869* (2017.08); *A61P 35/00* (2018.01); *C07K 16/30* (2013.01); *A61K 2039/505* (2013.01); *C07K 2317/24* (2013.01); *C07K 2317/565* (2013.01)

(56) References Cited

U.S. PATENT DOCUMENTS

| | | | |
|---|---|---|---|
| 2012/0251558 A1 | 10/2012 | Gerber et al. | |
| 2013/0295007 A1 | 11/2013 | Chen et al. | |
| 2018/0055948 A1 | 3/2018 | Huang et al. | |
| 2020/0255522 A1* | 8/2020 | Brinkmann | C07K 16/00 |

FOREIGN PATENT DOCUMENTS

| | | | |
|---|---|---|---|
| CN | 106177984 A | | 12/2016 |
| EP | 3 296 321 A1 | | 3/2018 |
| EP | 3 292 874 B1 | | 4/2020 |
| WO | WO 2017/031034 A2 | | 2/2017 |
| WO | WO 2017/17737 A1 | | 10/2017 |
| WO | WO 2018/036243 A1 | | 3/2018 |
| WO | 2019086362 | * | 5/2019 |
| WO | WO 2019/086362 A1 | | 5/2019 |

OTHER PUBLICATIONS

Chowdhury et al., Immunol. Jan. 1997;34(1):9-20 (Year: 1997).*
Celie et al., Current Opinion in Structural Biology 2016, 38: 145-154 (Year: 2016).*
Thomas et al., Nature Reviews Genetics vol. 4, pp. 346-358 (2003) (Year: 2003).*
Australian Examination Report for Application No. 2019272250, mailed Mar. 9, 2021.
International Search Report and Written Opinion mailed Aug. 5, 2019 for Application No. PCT/CN2019/086977.
Extended European Search Report for Application No. EP19808424.6, mailed Aug. 13, 2021.
Brinkmann et al., Cloning and expression of the recombinant FAb fragment of monoclonal antibody K1 that reacts with mesothelin present on mesotheliomas and ovarian cancers. Int J Cancer. May 16, 1997;71(4):638-44. doi: 10.1002/(sici)1097-0215(19970516)71:4<638::aid-ijc21>3.0.co;2-6.
Chang et al., Isolation and characterization of a monoclonal antibody, K1, reactive with ovarian cancers and normal mesothelium. Int J Cancer. Feb. 1, 1992;50(3):373-81. doi: 10.1002/ijc.2910500308.
Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.
Weekes et al., Phase I Study of DMOT4039A, an Antibody-Drug Conjugate Targeting Mesothelin, in Patients with Unresectable Pancreatic or Platinum-Resistant Ovarian Cancer. Mol Cancer Ther. Mar. 2016;15(3):439-47. doi: 10.1158/1535-7163.MCT-15-0693. Epub Jan. 28, 2016.
International Preliminary Report on Patentability for Application No. PCT/CN2019/086977, mailed Dec. 3, 2020.
Chang et al., Monoclonal antibody K1 reacts with epithelial mesothelioma but not with lung adenocarcinoma. Am J Surg Pathol. Mar. 1992;16(3):259-68. doi: 10.1097/00000478-199203000-00006.
Chowdhury et al., Isolation of a high-affinity stable single-chain Fv specific for mesothelin from DNA-immunized mice by phage display and construction of a recombinant immunotoxin with anti-tumor activity. Proc Natl Acad Sci U S A. Jan. 20, 1998;95(2):669-74. doi: 10.1073/pnas.95.2.669.
Chowdhury et al., Isolation of anti-mesothelin antibodies from a phage display library. Mol Immunol. Jan. 1997;34(1):9-20. doi: 10.1016/s0161-5890(97)00011-4.
Klampatsa et al., Mesothelin-targeted CAR-T cell therapy for solid Tumors. Expert Opin Biol Ther. Apr. 2021;21(4):473-486. doi: 10.1080/14712598.2021.1843628. Epub Nov. 12, 2020.

* cited by examiner

```
                         SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1

Gly Phe Asp Phe Ser Arg Tyr Trp Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 2

Glu Ile Asn Pro Asp Ser Ser Thr Ile Val Tyr Thr Pro Ser Leu Lys
1               5                   10                  15

Asp

<210> SEQ ID NO 3
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 3

Arg Gly Ser His Tyr Tyr Gly Tyr Arg Thr Gly Tyr Phe Asp
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 4

Ser Ala Ser Ser Ser Val Ser Tyr Met Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Asp Thr Ser Asn Leu Ala Ser
```

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 6

```
Gln Gln Trp Ser Ser Tyr Pro Pro Thr
1               5
```

<210> SEQ ID NO 7
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Val Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Arg Gly Ser His Tyr Tyr Gly Tyr Arg Thr Gly Tyr Phe Asp
            100                 105                 110

Val Trp Gly Ala Gly Thr Thr Val Thr Val Ser Ser
        115                 120
```

<210> SEQ ID NO 8
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 8

```
Asp Val Val Met Thr Gln Ser Pro Ala Phe Leu Ser Val Thr Pro Gly
1               5                   10                  15

Glu Lys Val Thr Met Thr Cys Ser Ala Ser Ser Val Ser Tyr Met
            20                  25                  30

Tyr Trp His Gln Gln Lys Pro Asp Gln Ala Pro Lys Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Asp Phe Thr Phe Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Val Glu Ile Lys
            100                 105
```

<210> SEQ ID NO 9
<211> LENGTH: 233
<212> TYPE: PRT
<213> ORGANISM: Artificial Sequence
<220> FEATURE:
<223> OTHER INFORMATION: Synthetic Polypeptide

<400> SEQUENCE: 9

```
Met Val Ser Pro Leu Gln Phe Leu Arg Leu Leu Leu Trp Val Pro
1               5                   10                  15

Ala Ser Arg Gly Asp Val Val Met Thr Gln Ser Pro Ala Phe Leu Ser
            20                  25                  30

Val Thr Pro Gly Glu Lys Val Thr Met Thr Cys Ser Ala Ser Ser
        35                  40                  45

Val Ser Tyr Met Tyr Trp His Gln Gln Lys Pro Asp Gln Ala Pro Lys
    50                  55                  60

Leu Leu Ile Tyr Asp Thr Ser Asn Leu Ala Ser Gly Val Pro Val Arg
65                  70                  75                  80

Phe Ser Gly Ser Gly Ser Gly Thr Asp Phe Thr Phe Thr Ile Ser Arg
                85                  90                  95

Met Glu Ala Glu Asp Ala Ala Thr Tyr Tyr Cys Gln Gln Trp Ser Ser
            100                 105                 110

Tyr Pro Pro Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 10
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 10

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asp Phe
        35                  40                  45

Ser Arg Tyr Trp Met Ser Trp Val Arg Gln Ala Pro Gly Lys Gly Leu
    50                  55                  60

Glu Trp Ile Gly Glu Ile Asn Pro Asp Ser Ser Thr Ile Val Tyr Thr
```

```
                65                  70                  75                  80
Pro Ser Leu Lys Asp Lys Phe Ile Ile Ser Arg Asp Asn Ala Lys Asn
                    85                  90                  95

Thr Leu Tyr Leu Gln Met Asn Ser Leu Arg Ala Glu Asp Thr Ala Leu
            100                 105                 110

Tyr Tyr Cys Ala Arg Arg Gly Ser His Tyr Tyr Gly Tyr Arg Thr Gly
        115                 120                 125

Tyr Phe Asp Val Trp Gly Ala Gly Thr Thr Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                    165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                    245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                    325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                    405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470
```

ANTI-MESOTHELIN ANTIBODY AND ANTIBODY DRUG CONJUGATE THEREOF

RELATED APPLICATIONS

This application is a national stage filing under 35 U.S.C. § 371 of International PCT Application, PCT/CN2019/086977, filed May 15, 2019, which claims priority to Chinese Application No. 201810487856.4, filed on May 21, 2018, the entire contents of each of which is incorporated herein by reference.

TECHNICAL FIELD

The present invention relates to an anti-mesothelin antibody or a functional fragment thereof. The invention also relates to an antibody drug conjugate comprising an anti-mesothelin antibody and a small molecule drug. The invention further relates to a use of the antibody and conjugate of the present invention in manufacture of a medicament for treatment of a tumor.

BACKGROUND ART

MSLN (Mesothelin) is an antigen recognized by monoclonal antibody CAK1 in mesothelial cells, mesothelioma and ovarian cancer. It is a 40 kDa cell surface glycoprotein with high expression in many tumor tissues, and thus is a very good target marker for therapeutic antibodies.

Although monoclonal antibodies have high therapeutic target specificity and low side effects, their efficacy is limited when used alone. Antibody drug conjugate is formed by linking a toxin with an antibody through a linker, and has both strong targeting ability and high-efficiency cytotoxicity, making the use of new ADC drug one of the most promising immunotherapy methods, and drawing much attention in cancer immunotherapy.

Some research groups have constructed antibody drug conjugates targeting MSLN, but these antibody drug conjugates still have many disadvantages, such as: coupling by thiol groups of cysteines on the antibody leads to the losing of original disulfide bond between peptide chains, and the resultant ADC is unstable, and once the ADC enters into the circulatory system, its half-life is shortened and the toxic-side effects thereof are significant; coupling by amino groups of lysines on the antibody makes the coupling sites random, which would affect the targeting ability of the antibody.

Therefore, there is still a need in the art to develop a MSLN antibody having more superior properties and an antibody drug conjugate comprising the antibody.

Contents of the Invention

The present invention provides an anti-mesothelin antibody or a functional fragment thereof, and an antibody drug conjugate comprising the antibody or a functional fragment thereof. In particular, the antibody drug conjugate of the invention has higher stability and lower toxic side effects, and/or has a higher affinity for mesothelin.

Specifically:

In one aspect, the present invention provides an antibody drug conjugate, wherein the antibody drug conjugate has the following structural formula:

$Ab\text{-}(L\text{-}D)_n$ wherein:
the Ab is an antibody or a functional fragment thereof that specifically binds to MSLN;
the L is empty or any linker;
the D is any therapeutic agent;
n is an integer selected from 1 to 8, such as 1, 2, 3, 4, 5, 6, 7 or 8, or an interval between any two thereof.

Further, the antibody of the present invention or a functional fragment thereof comprises a heavy chain and a light chain, wherein (i) the heavy chain comprises at least three CDR regions, wherein the amino acid sequence of at least one of the CDR regions has an amino acid sequence set forth in SEQ ID NO: 1, 2 or 3 or a sequence having at least 80% (preferably 85%, 90%, 95%, 98% or 99%) sequence identity thereto; and (ii) the light chain comprises at least three CDR regions, wherein the amino acid sequence of at least one of the CDR regions has an amino acid sequence set forth in SEQ ID NO: 4, 5 or 6 or a sequence having at least 80% (preferably 85%, 90%, 95%, 98% or 99%) sequences identity thereto. Preferably, the antibody of the present invention or a functional fragment thereof comprises a heavy chain and a light chain, wherein (i) the heavy chain variable region comprises three CDR regions, wherein the CDR regions have an amino acid sequence set forth in SEQ ID NO: 1, 2 or 3, respectively; and/or (ii) the light chain variable region comprises three CDR regions, wherein the CDR regions have an amino acid sequence set forth in SEQ ID NO: 4, 5 or 6, respectively. Most preferably, the CDRs of the heavy chain of the anti-mesothelin antibody disclosed in the present invention have an amino acid sequence set forth in SEQ ID NO: 1, SEQ ID NO: 2, and SEQ ID NO: 3, respectively, and the CDRs of the light chain variable region thereof have an amino acid sequence set forth in SEQ ID NO: 4, SEQ ID NO: 5, and SEQ ID NO: 6, respectively.

Further, the present invention provides an anti-mesothelin antibody or a functional fragment thereof comprising a heavy chain variable region and a light chain variable region, wherein (i) the heavy chain variable region comprises an amino acid sequence set forth in SEQ ID NO: 7 or a sequence having at least 80% (preferably 85%, 90%, 95%, 98% or 99%) sequence identity thereto; and (ii) the light chain variable region comprises an amino acid sequence set forth in SEQ ID NO: 8 or a sequence having at least 80% (preferably 85%, 90%, 95%, 98% or 99%) sequence identity thereto. Preferably, the antibody comprises a heavy chain and a light chain, wherein (i) the heavy chain variable region comprises an amino acid sequence set forth in SEQ ID NO: 7, and/or (ii) the light chain variable region comprises an amino acid sequence set forth in SEQ ID NO: 8. Most preferably, the heavy chain variable region of the anti-mesothelin antibody disclosed in the present invention comprises an amino acid sequence set forth in SEQ ID NO: 7, and the light chain variable region comprises an amino acid sequence set forth in SEQ ID NO: 8.

In certain specific embodiments, the antibody of the invention comprises a heavy chain and a light chain, wherein the heavy chain comprises an amino acid sequence set forth in SEQ ID NO: 10, and the light chain comprises an amino acid sequence set forth in SEQ ID NO:9.

In another aspect, the invention provides an antibody drug conjugate comprising an anti-mesothelin antibody or a functional fragment thereof, and a therapeutic agent. Preferably, the antibody drug conjugate of the invention further comprises a linker that links the anti-mesothelin antibody or a functional fragment thereof to a therapeutic agent.

In certain embodiments, the linker L of the present invention can be linked to the antibody by any means known in the art, preferably by a thiol group and/or an amino group. In a preferred embodiment, the antibody of the invention is linked to a linker by a thiol group on the antibody. The linker L of the present invention may be absent (i.e., the antibody is directly linked to the therapeutic agent D) or any one of cleavable (i.e., a linker that cleaves in an in vivo environment) or non-cleavable linkers or a combination thereof; preferably, the linker may be selected from those listed in Table 1 below.

TABLE 1

Linkers usable in the antibody conjugate of the present invention

| Abbreviation | Full name in Chinese/Full name in English |
| --- | --- |
| Mc | Maleimidocaproyl |
| Mc-Val-Cit-PAB | Maleimidocaproyl -valine -citrulline p-amino-benzyloxycarbonyl |
| Py | Triacryloylhexahydro triazine |
| Py-MAA-Val-Cit-PAB | Triacryloylhexahydro triazine-mercaptoacetic acid-valine-citrulline-p-amino-benzyloxycarbonyl |
| 3-MPA | 3-Maleimidopropionic acid |
| Mal-di-EG-OPFP | Perfluorophenyl-3-(2-(2-(3-(2,5-dioxo-2,5-dihydro-1H-Pyrrol-1-yl) propanamido) ethoxy)ethoxy)propanoate |
| Mal-di-EG-OSu | 2,5-dioxoPyrrolidin-a-yl 3-(2-(2-(2,5-dioxo-2,5-dihydro-1H-Pyrrol-1-yl) ethoxy)ethoxy)propanoate |
| Mal-Tri-EG-OSu | 2,5-dioxoPyrrolidin-a-yl 3-(2-(2-(2-(2,5-dioxo-2,5-dihydro-1H-Pyrrol-1-yl)ethoxy)ethoxy)ethoxy)propanoate |
| Mal-Tetra-EG-OSu | 2,5-dioxoPyrrolidin-a-yl 1-(2,5-dioxo-2,5-dihydro-1H-Pyrrol-1-yl)-3-oxo-7,10,13,16-tetraoxa-4-azanonadecan-19-oate |
| Br-di-EG-OSu | 2,5-dioxoPyrrolidin-a-yl 3-(2-(2-(2-bromoacetamido)ethoxy)ethoxy)propanoate |
| Py-ds-Prp-OSu | 2,5-dioxoPyrrolidin-1-yl 3-(Pyridin-2-yldisulfanyl)propanoate |
| Py-ds-Prp-OPFP | perfluorophenyl 3-(Pyridin-2-yldisulfanyl)propanoate |
| Py-ds-dmBut-OSu | 2,5-dioxoPyrrolidin-a-yl 4-methyl-4-(Pyridin-2-yldisulfanyl)pentanoate |
| Py-ds-dmBut-OPF | perfluorophenyl 4-methyl-4--(Pyridin-2-yldisulfanyl)propanoate |
| SMcC | N-succinimidyl 4-(maleimidomethyl)cyclohexanecarboxylate |
| MBS | 3-maleimidobenzoic acid N-hydroxysuccinimide ester |
| SATA | S-(N-succinimidyl)thioacetate |
| SPDP | N-succinimidyl 3-(2-Pyridyldithio)propionate |
| SMPT | (N-succinimidyloxy carbonyl)-1-methyl-1-(2-Pyridyldithio)toluene |

In some embodiments, the linker of the present invention is preferably selected from those listed in Table 2 below.

TABLE 2

Preferred linkers useful in the antibody conjugate of the present invention

| Abbreviation | Structure/Full name in Chinese/Full name in English |
| --- | --- |
| Mc-Val-Cit-PAB | maleimidocaproyl-valine-citrulline-p-aminobenzylcarbonyl |

TABLE 2-continued

Preferred linkers useful in the antibody conjugate of the present invention

| Abbreviation | Structure/Full name in Chinese/Full name in English |
|---|---|
| Py-MAA-Val-Cit-PAB | 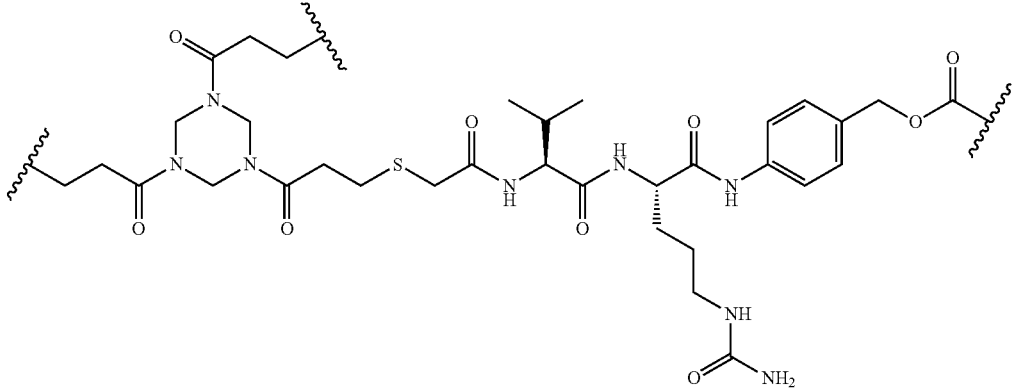<br>Triacryloylhexahydro triazine-mercaptoacetic acid-valine-citrulline-p-aminobenzyloxycarbonyl |
| Mc | 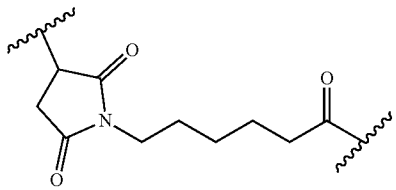<br>maleimidocaproyl |
| Py | 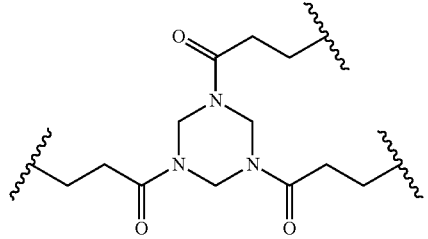<br>Triacryloylhexahydro triazine |

In some embodiments of the present invention, the therapeutic agent D is selected from the group consisting of: maytansine compounds, V-ATPase inhibitors, pro-apoptotic agents, Be 12 inhibitors, McL1 inhibitors, HSP90 inhibitors, IAP inhibitors, mTOr inhibitors, microtubule stabilizers, microtubule destabilizers, auristatin, dolastatin, MetAP (methionine aminopeptidase), protein CRM1 nuclear export inhibitors, DPPIV inhibitors, proteasome inhibitors, inhibitors of phosphoryl transfer reaction in mitochondria, protein synthesis inhibitors, kinase inhibitors, CDK2 inhibitors, CDK9 inhibitors, kinesin inhibitors, HDAC inhibitors, DNA damage agents, DNA alkylating agents, DNA intercalators, DNA minor groove binders, DHFR inhibitors, and dolastatin peptides.

In some preferred embodiments of the invention, the therapeutic agent D is a cytotoxic substance (e.g., an antimetabolite, an antitumor antibiotic, an alkaloid), an immunopotentiator, or a radioisotope. Preferably, the therapeutic agent D may be selected from the group consisting of MMAD (monomethyl auristatin D) and its derivatives, MMAE (monomethyl auristatin E) and its derivatives, MMAF (monomethyl auristatin F) and its derivatives, Mertansine derivative M1, Mertansine derivative M4, Duocarmycine, Calicheamicin, PBDA (pyrrolobenzodiazepines), Doxorubicin, Vinca Alkaloids, Metrotrexate, Vinblastine, Daunorubicin; more preferably, the therapeutic agent is selected from maytansinoids (e.g., Ansamitocin or Mertansine), dolastatin and its derivatives; most preferably, the therapeutic agent is selected from the group consisting of MMAD and MMAE.

In certain embodiments, the present invention relates to an antibody drug conjugate of the general formula Ab-(L-D)$_n$, wherein Ab is any anti-mesothelin antibody of the present invention, and L is selected from the group consisting of Py-MAA-Val-Cit-PAB, Mc-Val-Cit-PAB, D is selected from MMAD or MMAE, and n is an integer selected from 1 to 8, such as 1, 2, 3, 4, 5, 6, 7, 8 or an interval between any two thereof.

In certain specific embodiments, the antibody drug conjugate of the invention has a structure as shown in any of the following formulas:

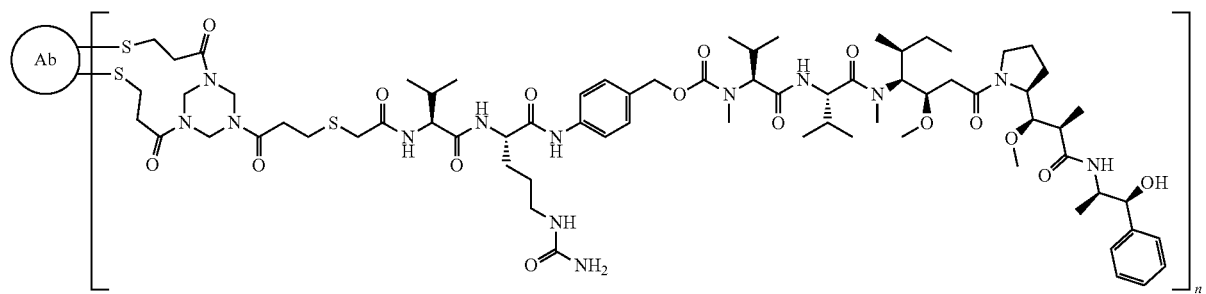

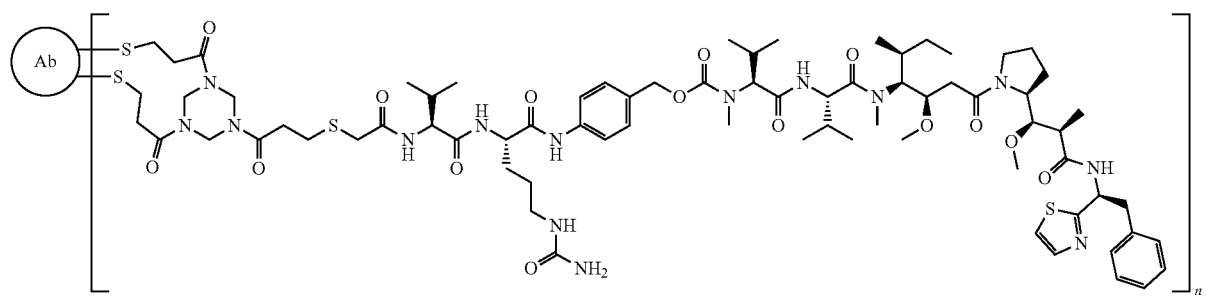

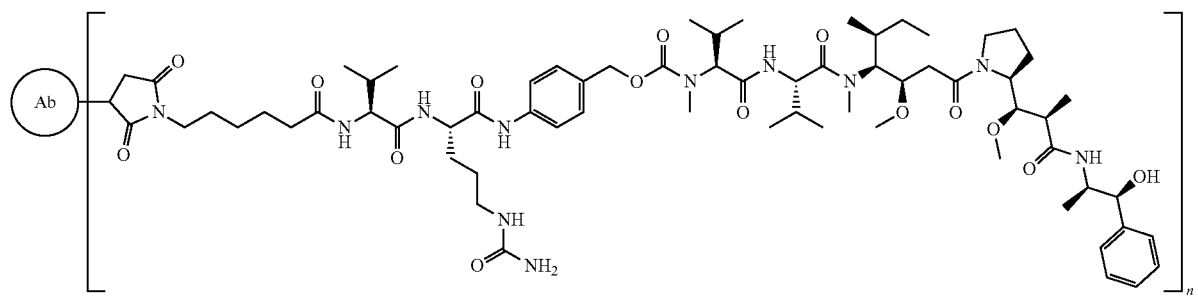

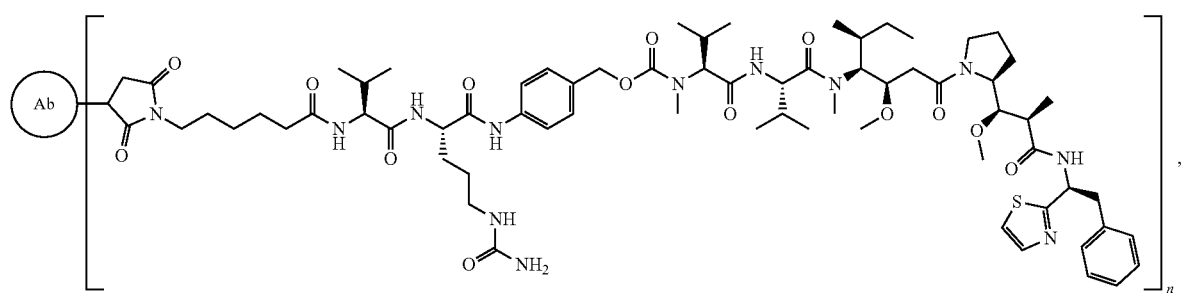

wherein n is 1, 2, 3, 4, 5, 6, 7 or 8.

In particular, the present invention relates to an antibody drug conjugate of the general formula Ab-(L-D)n, wherein Ab is any anti-mesothelin antibody of the present invention, the heavy chain variable region CDRs of the antibody have an amino acid sequence set forth in SEQ ID NO: 1, SEQ ID NO: 2, and SEQ ID NO: 3, respectively, and the light chain variable region CDRs of the antibody have an amino acid sequence set forth in SEQ ID NO: 4, SEQ ID NO: 5, and SEQ ID NO: 6, respectively; L is Py-MAA-Val-Cit-PAB, and D is MMAE. More particularly, the antibody drug conjugate of the present invention is RC88-Py-MAA-Val-Cit-PAB-MMAE having the structure shown by the following formula, wherein n is 1, 2, 3, 4, 5, 6, 7 or 8:

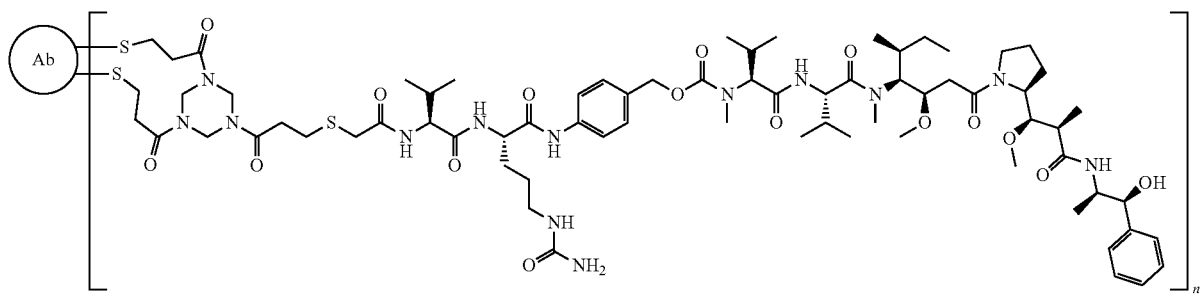

RC88-Py-MAA-Val-Cit-PAB-MMAE

In particular, the present invention relates to an antibody drug conjugate of the general formula Ab-(L-D)$_n$, wherein Ab is any anti-mesothelin antibody of the present invention, the heavy chain variable region CDRs of the antibody have an amino acid sequence set forth in SEQ ID NO: 1, SEQ ID NO: 2, and SEQ ID NO: 3, respectively, and the light chain variable region CDRs of the antibody have an amino acid sequence set forth in SEQ ID NO: 4, SEQ ID NO: 5, and SEQ ID NO: 6, respectively; L is Py-MAA-Val-Cit-PAB, and D is MMAD. More particularly, the antibody drug conjugate of the present invention is RC88-Py-MAA-Val-Cit-PAB-MMAD having the structure shown by the following formula, wherein n is 1, 2, 3, 4, 5, 6, 7 or 8:

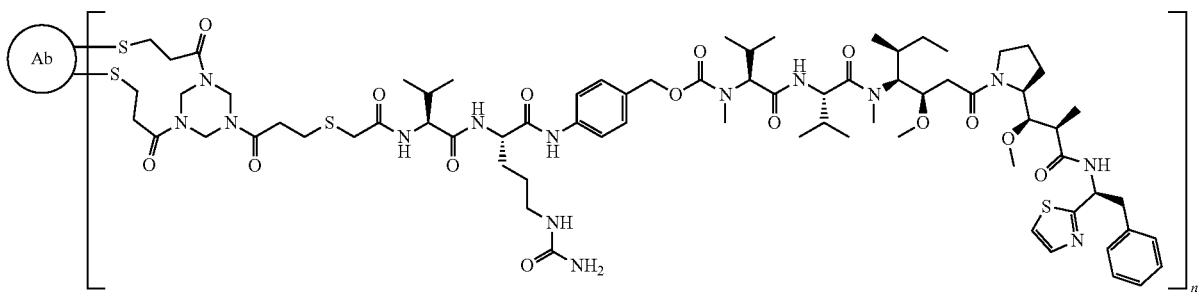

RC88-Py-MAA-Val-Cit-PAB-MMAD

In particular, the present invention relates to an antibody drug conjugate of the general formula Ab-(L-D)$_n$, wherein Ab is any anti-mesothelin antibody of the present invention, the heavy chain variable region CDRs of the antibody have an amino acid sequence set forth in SEQ ID NO: 1, SEQ ID NO: 2, and SEQ ID NO: 3, respectively, and the light chain variable region CDRs of the antibody have an amino acid sequence set forth in SEQ ID NO: 4, SEQ ID NO: 5, and SEQ ID NO: 6, respectively; L is Mc-Val-Cit-PAB, and D is MMAE. More particularly, the antibody drug conjugate of the present invention is RC88-Mc-Val-Cit-PAB-MMAE having the structure shown by the following formula, wherein n is 1, 2, 3, 4, 5, 6, 7 or 8:

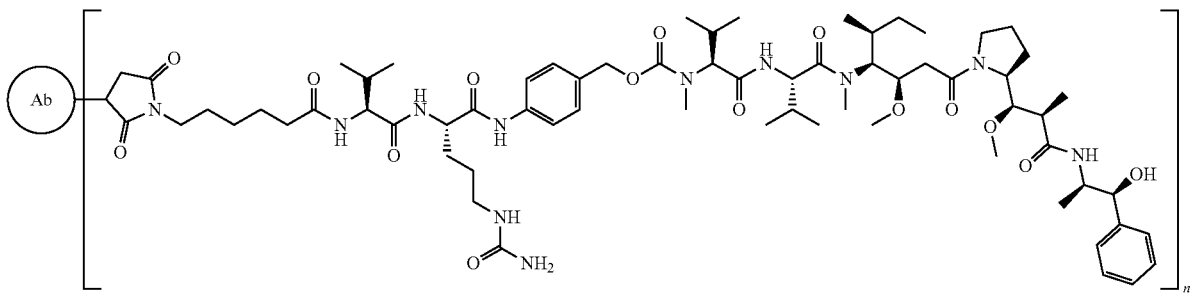

RC88-Mc-Val-Cit-PAB-MMAE

In particular, the present invention relates to an antibody drug conjugate of the general formula Ab-(L-D)$_n$, wherein Ab is any anti-mesothelin antibody of the present invention, the heavy chain variable region CDRs of the antibody have an amino acid sequence set forth in SEQ ID NO: 1, SEQ ID NO: 2, and SEQ ID NO: 3, respectively, and the light chain variable region CDRs of the antibody have an amino acid sequence set forth in SEQ ID NO: 4, SEQ ID NO: 5, and SEQ ID NO: 6, respectively; L is Mc-Val-Cit-PAB, and D is MMAD. More particularly, the antibody drug conjugate of the present invention is RC88-Mc-Val-Cit-PAB-MMAD having the structure shown by the following formula, wherein n is 1, 2, 3, 4, 5, 6, 7 or 8:

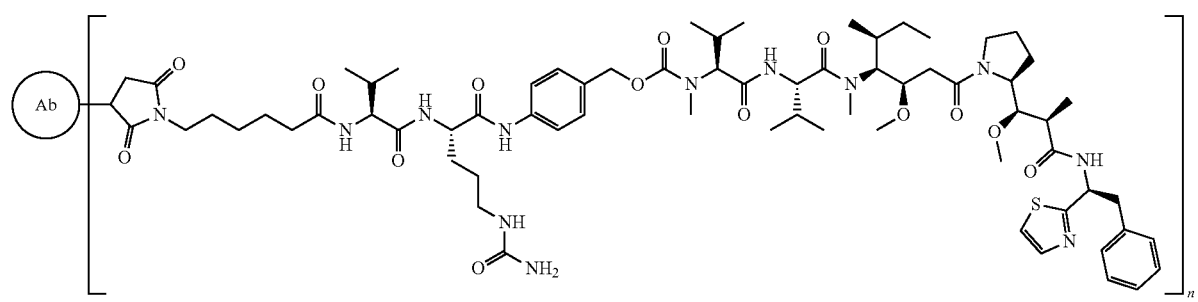

RC88-Mc-Val-Cit-PAB-MMAD

In particular, the present invention relates to an antibody drug conjugate of the general formula Ab-(L-D)$_n$, wherein Ab is any anti-mesothelin antibody of the present invention, the antibody has a heavy chain variable region sequence set forth in SEQ ID NO: 7 and a light chain variable region sequence set forth in SEQ ID NO: 8; Lis Py-MAA-Val-Cit-PAB, and Dis MMAE. More particularly, the antibody drug conjugate of the present invention is RC88-Py-MAA-Val-Cit-PAB-MMAE having the structure shown by the following formula, wherein n is 1, 2, 3, 4, 5, 6, 7 or 8:

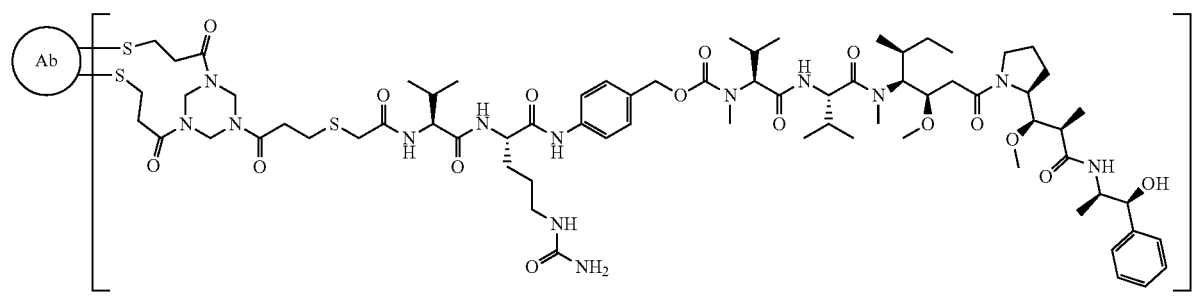

RC88-Py-MAA-Val-Cit-PAB-MMAE

In particular, the present invention relates to an antibody drug conjugate of the general formula Ab-(L-D)$_n$, wherein Ab is any anti-mesothelin antibody of the present invention, the antibody has a heavy chain variable region sequence set forth in SEQ ID NO: 7 and a light chain variable region sequence set forth in SEQ ID NO: 8; L is Py-MAA-Val-Cit-PAB, and D is MMAD. More particularly, the antibody drug conjugate of the present invention is RC88-Py-MAA-Val-Cit-PAB-MMAD having the structure shown by the following formula, wherein n is 1, 2, 3, 4, 5, 6, 7 or 8:

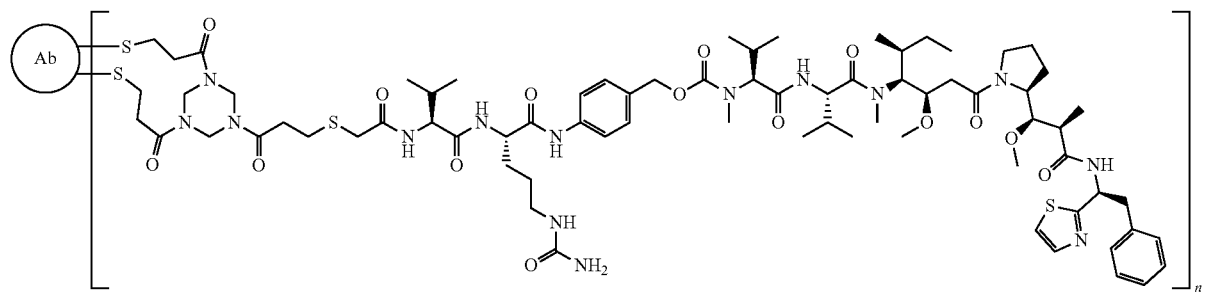

RC88-Py-MAA-Val-Cit-PAB-MMAD

In particular, the present invention relates to an antibody drug conjugate of the general formula Ab-(L-D)$_n$, wherein Ab is any anti-mesothelin antibody of the present invention, the antibody has a heavy chain variable region sequence set forth in SEQ ID NO: 7 and a light chain variable region sequence set forth in SEQ ID NO: 8; L is Mc-Val-Cit-PAB, and D is MMAE. More particularly, the antibody drug conjugate of the present invention is RC88-Mc-Val-Cit-PAB-MMAE having the structure shown by the following formula, wherein n is 1, 2, 3, 4, 5, 6, 7 or 8:

RC88-Mc-Val-Cit-PAB-MMAD

In another aspect, the present invention provides an antibody or a functional fragment thereof capable of binding mesothelin, wherein the antibody or a functional fragment thereof comprises a heavy chain and a light chain, wherein (i) the heavy chain comprises at least three CDR regions, wherein the amino acid sequence of at least one of the CDR regions has an amino acid sequence set forth in SEQ ID NO: 1, 2 or 3, or has a sequence having at least 80% (preferably 85%, 90%, 95%, 98% or 99%) sequence identity thereto; and/or

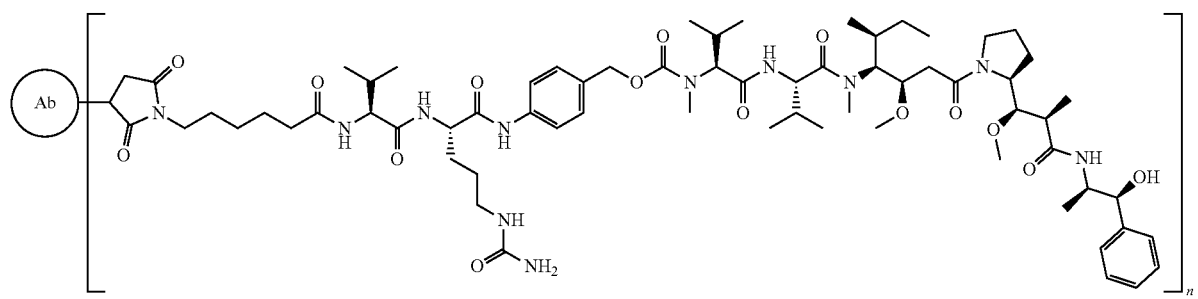

RC88-Mc-Val-Cit-PAB-MMAE

In particular, the present invention relates to an antibody drug conjugate of the general formula Ab-(L-D)$_n$, wherein Ab is any anti-mesothelin antibody of the present invention, the antibody has a heavy chain variable region sequence set forth in SEQ ID NO: 7 and a light chain variable region sequence set forth in SEQ ID NO: 8; L is Mc-Val-Cit-PAB, and D is MMAD. More particularly, the antibody drug conjugate of the present invention is RC88-Mc-Val-Cit-PAB-MMAD having the structure shown by the following formula, wherein n is 1, 2, 3, 4, 5, 6, 7 or 8:

(ii) the light chain comprises at least three CDR regions, wherein the amino acid sequence of at least one of the CDR regions has an amino acid sequence set forth in SEQ ID NO: 4, 5 or 6, or has a sequence having at least 80% (preferably 85%, 90%, 95%, 98% or 99%) sequence identity thereto.

In certain specific embodiments, the anti-mesothelin antibody or a functional fragment thereof of the present invention comprises a heavy chain and a light chain, wherein:

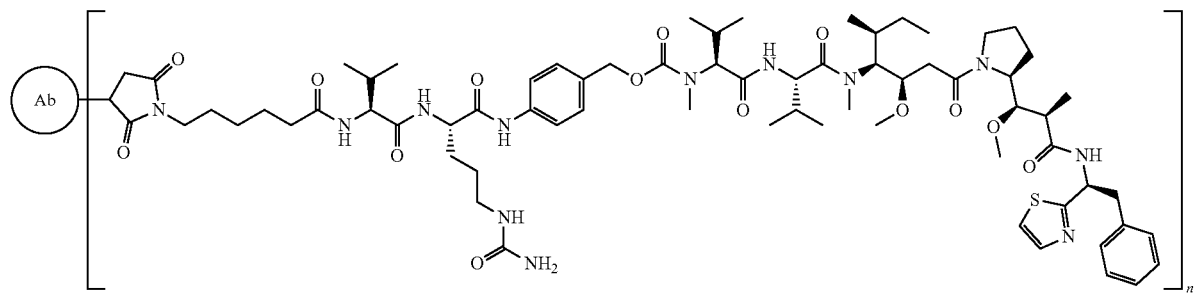

(i) the heavy chain variable region comprises three CDR regions, wherein the CDR regions have an amino acid sequence as set forth in SEQ ID NO: 1, 2 or 3, respectively; and/or (ii) the light chain variable region comprises three CDR regions, wherein the CDR regions have an amino acid sequence as set forth in SEQ ID NO: 4, 5 or 6, respectively.

In particular, the amino acid sequences of the heavy chain CDR regions of the anti-mesothelin antibody disclosed in the present invention are set forth in SEQ ID NO: 1, SEQ ID NO: 2, and SEQ ID NO: 3, respectively.

In particular, the amino acid sequences of the light chain CDR regions of the anti-mesothelin antibody disclosed in the present invention are shown in SEQ ID NO: 4, SEQ ID NO: 5, and SEQ ID NO: 6, respectively.

More specifically, in the anti-mesothelin antibody disclosed in the present invention, the amino acid sequences of the heavy chain CDR regions thereof are set forth in SEQ ID NO: 1, SEQ ID NO: 2, and SEQ ID NO: 3, respectively, and the amino acid sequences of the light chain variable region CDR regions thereof are set forth in SEQ ID NO: 4, SEQ ID NO: 5, and SEQ ID NO: 6, respectively.

In a further aspect, the present invention provides an anti-mesothelin antibody or a functional fragment thereof, which comprises a heavy chain and a light chain, wherein the heavy chain and the light chain comprise a heavy chain variable region and a light chain variable region, respectively:

(i) the heavy chain variable region comprises an amino acid sequence set forth in SEQ ID NO: 7, or a sequence having at least 80% (preferably 85%, 90%, 95%, 98% or 99%) sequence identity thereto; and (ii) the light chain variable region comprises an amino acid sequence set forth in SEQ ID NO: 8, or a sequence having at least 80% (preferably 85%, 90%, 95%, 98% or 99%) sequence identity thereto.

In certain specific embodiments, the antibody comprises a heavy chain and a light chain, wherein the heavy chain and the light chain comprise a heavy chain variable region and a light chain variable region, respectively, wherein (i) the heavy chain variable region comprises an amino acid sequence set forth in SEQ ID NO: 7, and/or (ii) the light chain variable region comprises an amino acid sequence set forth in SEQ ID NO: 8.

In particular, the anti-mesothelin antibody of the present invention comprises a heavy chain and a light chain, wherein the heavy chain and the light chain comprise the amino acid sequences set forth in SEQ ID NO: 10 and SEQ ID NO: 9, respectively.

In certain specific embodiments, the anti-mesothelin antibody or a functional fragment thereof is isolated.

In certain specific embodiments, the anti-mesothelin antibody or a functional fragment thereof is a monoclonal antibody, a chimeric antibody, a humanized antibody, a human antibody, a single chain antibody (scFv) or a bispecific antibody; in certain specific embodiments, the anti-mesothelin antibody or a functional fragment thereof is a monoclonal antibody; in certain specific embodiments, the anti-mesothelin antibody or a functional fragment thereof is a humanized antibody; in certain specific embodiments, the anti-mesothelin antibody or a functional fragment thereof is an IgGIκ antibody.

In a further aspect, the invention provides an isolated polynucleotide encoding an antibody of the present invention.

In a further aspect, the invention provides a combination of isolated polynucleotides, the combination comprising a polynucleotide encoding a light chain of the antibody of the present invention or a functional fragment thereof, and a polynucleotide encoding a heavy chain of the antibody of the invention or a functional fragment thereof.

In a further aspect, the invention provides an expression vector or a combination of expression vectors, which comprises a polynucleotide according to the present invention or a combination of polynucleotides according to the present invention, the polynucleotide is operably linked to a regulatory sequence in a host cell or a cell-free expression system allowing the expression of the polypeptide encoded thereby.

In a further aspect, the invention provides a pharmaceutical composition comprising an antibody or a functional fragment thereof according to the present invention, and/or a conjugate according to the present invention, and a pharmaceutically acceptable carrier.

In a further aspect, the invention provides a method of treating or preventing a cancer, comprising administering to a subject in need thereof a therapeutically effective amount of the antibody, polynucleotide, combination of polynucleotides, expression vector, conjugate and/or pharmaceutical composition, according to the present invention.

In a further aspect, the invention provides a use of the antibody, polynucleotide, combination of polynucleotides, expression vector, conjugate and/or pharmaceutical composition, according to the present invention, in manufacture of a medicament for the treatment or prevention of a cancer.

In a further aspect, the invention provides the antibody, polynucleotide, combination of polynucleotides, expression vector, conjugate and/or pharmaceutical composition, according to the present invention, for use in the treatment or prevention of a cancer.

In a further aspect, the invention provides a use of the antibody drug conjugate of any one of the above embodiments in manufacture of a medicament for the treatment of a cancer.

In certain specific embodiments, the cancer of the invention is a mesothelin-positive cancer.

SPECIFIC MODELS FOR CARRYING OUT THE INVENTION

Definition

Figure 1:
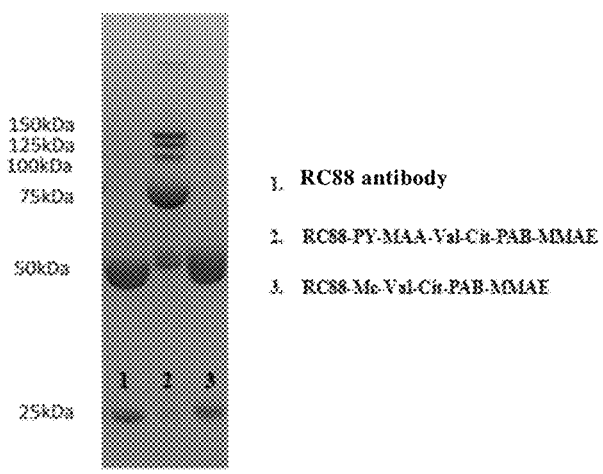
FIG. 1 shows SDS-PAGE characterization diagrams of RC88-PY-MAA-Val-Cit-PAB-MMAE and RC88-Mc-Val-Cit-PAB-MMAE, which characterized the coupling of RC88 antibody with linker and drug conjugate.

Unless otherwise defined, all technical and scientific terms used herein have the same meaning as understood by one of ordinary skill in the art. For the specific definitions and terminology in the art, the professional can refer to Current Protocols in Molecular Biology (Ausubel). Abbreviations for amino acid residues are standard 3-letter and/or 1-letter codes used in the art to refer to one of the 20 commonly used L-amino acids.

Although numerical ranges and parameter approximations in broad scopes are shown in the present invention, the numerical values in the specific embodiments are described as accurately as possible. However, any numerical value inherently contains certain errors due to the standard deviations present in their respective measurements. In addition, all ranges disclosed herein are to be understood as encompassing any and all sub-ranges. For example, the recited range of "1 to 10" should be considered to encompass any and all sub-ranges between the minimum 1 and the maximum 10 (including the endpoints); that are, all sub-ranges starting with minimum of 1 or greater, e.g., 1 to 6.1, and sub-ranges ending at maximum of 10 or less, e.g., 5.5 to 10. In addition, any reference that is referred to as "incorporated herein" is understood to be incorporated in its entirety.

It should be further noted that, as used in the description, the singular form of an object to which it refers would encompass its plural form, unless explicitly and clearly limited to one of the object. The term "or" can be used interchangeably with the term "and/or", unless the context clearly dictates otherwise.

The term "mesothelin", also known as MSLN, as used herein, refers to any natural, mature mesothelin derived from the processing of cellular mesothelin precursor proteins. The term encompasses mesothelin from any vertebrate source, including mammals such as primates (e.g., humans, apes and monkeys) and rodents (e.g., mice and rats), unless otherwise stated; and the term also encompasses any naturally occurring variant, such as splice variant or allelic variant, of mesothelin.

As used herein, the terms "pharmaceutical composition", "combination drug" and "drug combination" are used interchangeably and mean at least one drug and optionally a pharmaceutically acceptable carrier or excipient that are combined together to achieve a particular purpose. In certain embodiments, the pharmaceutical composition includes a combination that is separated in time and/or space, as long as being capable of acting together to achieve the purpose of the present invention. For example, the components (e.g., antibodies, nucleic acid molecules, nucleic acid molecule combinations, and/or conjugates according to the invention) contained in the pharmaceutical composition can be administered to a subject as a whole or separately to the subject. When the components contained in the pharmaceutical composition are separately administered to a subject, the components may be administered to the subject simultaneously or sequentially. Preferably, the pharmaceutically acceptable carrier is water, a buffered aqueous solution, an isotonic saline solution such as PBS (phosphate buffer), glucose, mannitol, dextrose, lactose, starch, magnesium stearate, cellulose, magnesium carbonate, 0.3% glycerol, hyaluronic acid, ethanol or polyalkylene glycols such as polypropylene glycol, triglycerides and the like. The type of the used pharmaceutically acceptable carrier especially depends on whether the composition according to the present invention is formulated for oral, nasal, intradermal, subcutaneous, intramuscular or intravenous administration. The composition according to the present invention may comprise a wetting agent, an emulsifier or a buffer substance as an additive.

The pharmaceutical composition, vaccine or pharmaceutical preparation according to the present invention may be administered via any suitable route, for example, oral, nasal, intradermal, subcutaneous, intramuscular or intravenous administration.

The term "therapeutic agent" used herein refers to any substance or entity that could exert therapeutic effect (e.g., treatment, prevention, amelioration or inhibition of any disease and/or disorder), includes but is not limited to: chemotherapy agents, radiotherapy agents, immunotherapeutic agents, thermal therapeutic agents, and the like.

As used herein, "CDR region" or "CDR" refers to a hypervariable region of the heavy chain and light chain of an immunoglobulin, as defined by Kabat et al. (Kabat et al., Sequences of proteins of immunological interest, 5th Ed., U.S. Department of Health and Human Services, NIH, 1991, and later versions). There are three heavy chain CDRs and three light chain CDRs. The term CDR or CDRs as used herein is used to indicate one of these regions, or a few or even all of these regions, which contain a majority of the amino acid residues responsible for binding by the affinity of the antibody to an antigen or its recognition epitope.

For the purposes of the present invention, "consistency", "identity" or "similarity" between two nucleic acid or amino acid sequences refers to the percentage of identical nucleotides or identical amino acid residues between two sequences to be compared that is obtained after optimal alignment, wherein the percentage is purely statistical and the differences between the two sequences are randomly distributed and covering their full length. The sequence comparison between two nucleic acid or amino acid sequences is typically performed by comparing the sequences after they have been optimally aligned, and the comparison can be performed by segments or "comparison window". In addition to being performed manually, the optimal alignment for comparing sequences can be performed by the local homology algorithm of Smith and Waterman (1981) [Ad. App. Math. 2:482], by the local homology algorithm of Neddleman and Wunsch (1970). [J. Mol. Biol. 48:443], by the similarity search method of Pearson and Lipman (1988) [Proc. Natl. Acad. Sci. USA 85:2444), or by computer software (GAP, BESTFIT, FASTA and TFASTA in the Wisconsin Genetics Software Package, Genetics Computer Group, 575 Science Dr., Madison, WI, or by BLAST N or BLAST P comparison software) using these algorithms.

As used herein, "therapeutically effective amount" or "effective amount" refers to a dose sufficient to demonstrate its benefit to a subject to which it is administered. The actual amount administered, as well as the rate and time course of administration, will depend on the condition and severity of the subject to be treated. The prescription for treatment (e.g., determination of dose, etc.) is ultimately the responsibility of a general medical practitioner and other physicians and depends on their decision, usually considering the disease being treated, the condition of individual patient, the site of delivery, the method of administration, and other known factors.

The term "subject" as used herein refers to a mammal, such as a human, but may also be other animals, such as a wild animal (such as a heron, a stork, a crane, etc.), a livestock (such as a duck, a goose, etc.) or an experimental animal (such as an orangutan, a monkey, a rat, a mouse, a rabbit, a guinea pig, a woodchuck, a ground squirrel, etc.).

As used herein, "antibody" is used in its broadest sense and encompasses a variety of antibody structures, including but not limited to, monoclonal antibodies, polyclonal antibodies, multispecific antibodies (e.g., bispecific antibodies), and antibody fragments, in particular, "antibody" as used herein refers to a protein comprising at least two heavy (H) chains and two light (L) chains interconnected by disulfide bonds. Each heavy chain comprises a heavy chain variable region (abbreviated as VH) and a heavy chain constant region. The heavy chain constant region comprises three domains (CH1, CH2 and CH3). Each light chain comprises a light chain variable region (abbreviated as VL) and a light chain constant region. The light chain constant region contains one domain (CL). The VH and VL regions can also be subdivided into a plurality of regions with high variability, which are referred to as complementarity determining regions (CDRs), interspersed with more conservative regions called framework regions (FRs). Each VH and VL consists of three CDRs and four FRs, arranged from amino terminus to carboxy terminus in the following order: FR1, CDR1, FR2, CDR2, FR3, CDR3, FR4. These variable regions of the heavy chains and light chains comprise a binding domain that interacts with an antigen. The constant region of antibody mediates the binding of immunoglobulin to a host's tissue or factor, including the various cells of immune system (such as effector cells) and the first component (Clq) of classical complement system. Chimeric or humanized antibodies are also encompassed in the antibodies according to the present invention.

The term "humanized antibody" refers to an antibody comprising a CDR region derived from a non-human antibody, and the other portion of the antibody molecule is derived from one (or several) human antibodies. Moreover, in order to retain binding affinity, some residues of the framework region (referred to as FR) segment can be modified (Jones et al., Nature, 321:522-525, 1986; Verhoeyen et al., Science, 239:1534-1536, 1988; Riechmann et al., Nature, 332:323-327, 1988). the humanized antibody or fragments thereof according to the present invention can be prepared by the techniques known to those skilled in the art (for example, as described in the following documents: Singer et al., J. Immun. 150:2844-2857, 1992; Mountain et al., Biotechnol. Genct. Eng. Rev., 10:1-142, 1992; or Bebbington et al., Bio/Technology, 10:169-175, 1992).

The term "chimeric antibody" refers to an antibody wherein its variable region sequence is from one species and its constant region sequence is from another species, e.g., the variable region sequence is derived from a mouse antibody and the constant region sequence is derived from a human antibody. The chimeric antibody or a fragment thereof according to the present invention can be prepared by using genetic recombination techniques. For example, the chimeric antibody can be produced by cloning recombinant DNA comprising a promoter, a sequence encoding a variable region of a non-human, particularly murine, monoclonal antibody according to the present invention, and a sequence encoding a constant region of a human antibody. The chimeric antibody of the present invention encoded by such recombinant gene can be, for example, a murine-human chimera, the specificity of which is determined by the variable region derived from the murine DNA, and the isotype of which is determined by the constant region derived from the human DNA. The methods for preparing chimeric antibodies can refer to, for example, the document of Verhocyn et al., (BioEssays, 8:74, 1988).

The term "monoclonal antibody" refers to a preparation of an antibody molecule with single molecular composition. The monoclonal antibody composition shows single binding specificity and affinity for a particular epitope.

The term "functional fragment" as used herein refers to an antibody fragment consisting of or comprising a partial sequence of a heavy or light variable chain of the antibody from which it is derived, the partial sequence is sufficient to retain the same binding specificity and sufficient affinity as the antibody from which it is derived; preferably, shows an affinity at least equal to $1/100$ of that of the antibody from which it is derived; and more preferably, at least equal to $1/10$. Such a functional fragment comprises a minimum of 5 amino acids, preferably 10, 15, 25, 50 and 100 contiguous amino acids, of the antibody sequence from which it is derived.

The term "DAR" as used herein refers to the Drug-Antibody Ratio in an antibody drug conjugate, which represents the average number of drug molecules conjugated to one antibody. Preferably, the antibody drug conjugates of the present invention have a DAR value of from about 2 to about 6, such as about 2, 2.5, 3, 3.5, 3.6, 3.7, 3.8, 3.9, 4, 4.1, 4.2, 4.3, 4.4, 4.5, 5, 5.5, 6, or any interval between them.

In general, in order to prepare the monoclonal antibody or a functional fragment thereof, especially murine monoclonal antibody or a functional fragments thereof, reference may be made to techniques specifically described in the manual "Antibodies" (Harlow and Lane, Antibodies: A Laboratory Manual, Cold Spring Harbor Laboratory, Cold Spring Harbor NY, pp. 726, 1988) or the techniques of preparation from hybridoma cells as described by Kohler and Milstein (Nature, 256:495-497, 1975).

The monoclonal antibody or antibody drug conjugate according to the present invention may be purified, for example, may be purified on an affinity column, in which a MSLN antigen or one of its fragments that contains the epitope specifically recognized by the antibody according to the present invention has been immobilized on the affinity column in advance. More specifically, the monoclonal antibody can be purified by a protein A and/or G chromatography connected with or not an ion exchange chromatography for the purpose of eliminating residual protein contaminants and DNA and LPS, and itself is connected with or not an exclusion chromatography on Sepharose gels to eliminate potential aggregates due to the presence of dimers or other multimers. In more preferred embodiments, all of these techniques can be used simultaneously or continuously.

The term "dolastatin" as used herein refers to a polypeptide isolated from a marine organism, Dollabella auricularia, including but not limited to dolastatin 10 and dolastatin 15. The dolastatin peptides are mitotic inhibitors which exhibit strong anticancer activity and are therefore candidates for anticancer drugs. Researchers have further discovered and synthesized a number of derivatives of the dolastatin peptides, such as MMAE and MMAF.

The term "linker" as used herein refers to a portion of an antibody drug conjugate (i.e., ADC) that links an antibody to a drug, and it may be cleavable or non-cleavable. The cleavable linker (i.e., a linker that can cleave or a linker that can be biodegraded) can cleave within or on a target cell to release the drug. In certain embodiments, the linker of the invention has very good stability, greatly reducing the release of drug during the delivery (e.g., in the blood) to a target, thereby reducing side effects and toxicity. In some particular embodiments, the linker of the present invention is selected from a cleavable linker, such as a disulfide-based linker (which selectively cleaves in a tumor cell with a higher concentration of sulfhydryl group), a peptide linker (which is cleaved by an enzyme in a tumor cell), a hydrazone linker. In other specific embodiments, the linker of the present invention is selected from a non-cleavable linker (i.e., a linker that cannot cleave), such as a thioether linker. In still other embodiments, the linker of the present invention is a combination of a cleavable linker and a non-cleavable linker. Preferably, the linker of the present invention is selected from the group consisting of Mc-Val-Cit-PAB and Py-MAA-Val-Cit-PAB.

Anti-MSLN Antibody

The antibody in the antibody drug conjugate of the invention is characterized by specifically binds to a human MSLN. Preferably, the antibody binds to MSLN with a high affinity, for example, with a $K_D$ of $1\times10^{-7}$ M or less. The anti-MSLN antibody preferably exhibits one or more of the following characteristics:

(a) binding to a human MSLN at a $K_D$ of $1\times10^{-7}$ M or less (for example, $5\times10^{-8}$ M or less, $2\times10^{-8}$ M or less, $5\times10^{-9}$ M or less, $4\times10^{-9}$ M or less, $3\times10^{-9}$ M or less, $2\times10^{-9}$ M or less);

(b) binding to an Oval-Citar-3 cell with a high expression of MSLN, for example, at an $EC_{50}$ of 2000 ng/ml or less (e.g., 1000 ng/ml or less, 500 ng/ml or less, 400 ng/ml or less, 300 ng/ml or less, 250 ng/ml or less, 200 ng/ml or less, 150 ng/ml or less, 100 ng/ml or less, 50 ng/ml or less, 40 ng/ml or less, 30 ng/ml or less, 20 ng/ml or less, 10 ng/ml or less, 5 ng/ml or less), preferably the $EC_{50}$ is determined by using a flow cytometry method or an ELISA method; and (c) inhibiting in vivo growth of a cell that expresses MSLN.

Monoclonal Antibody RC88

The antibody preferably used in the antibody drug conjugate of the present invention is a human monoclonal antibody RC88. The VH and VL amino acid sequences of RC88 are shown in SEQ ID NOs: 7 and 8, respectively.

In another aspect, the antibody of the invention can comprise the heavy chain and light chain CDR1. CDR2 and CDR3 of RC88, or a combination thereof. The amino acid sequences of VHCDR1, VHCDR2 and VHCDR3 of RC88 are shown in SEQ ID NOs: 1-3, respectively. The amino acid sequences of VLCDR1, VLCDR2 and VLCDR3 of RC88 are shown in SEQ ID NOs: 4-6, respectively. The CDR regions are described using the Kabat system (Kabat, E. A., et al., (1991). Sequences of Proteins of Immunological Interest, Fifth Edition, U.S. Department of Health and Human Services, NIH Publication NO: 91-3242; hereinafter referred as "Kabat'3242").

EXAMPLE

The following are examples of the methods and compositions of the present invention. It should be understood that various other embodiments may be implemented in light of the above definitions and general descriptions.

Example 1: Anti-Mesothelin Antibody

Immunized animals were produced using standard methods to produce anti-mesothelin antibodies of the present invention, and the references were, for example, Kohler & Milstein, (1975) Nature 256:495-497, Kozbor et al. (1983) Immunol. Today 4:72, and Cole, et al. in MONOCLONAL ANTIBODIES AND CANCER THERAPY, Alan R. Liss, Inc., 1985, pp. 77-96.

Mesothelin was separated from the cells and purified by known techniques and used as an immunogen for immunization of animals, and the references were, for example, Zola, MONOCLONAL ANTIBODIES: PREPARATION AND USE OF MONOCLONAL ANTIBODIES AND ENGINEERED ANTIBODY DERIVATIVES (BASICS: FROM BACKGROUND TO BENCH) Springer-Verlag Ltd., New York, 2000; BASIC METHODS IN ANTIBODY PRODUCTION AND CHARACTERIZATION, Chapter 11, "Antibody Purification Methods," Howard and Bethell, Eds., CRC Press, 2000; ANTIBODY ENGINEERING (SPRINGER LAB MANUAL.), Kontermann and Dubel, Eds., Springer-Verlag, 2001.

Splenocytes were taken from the immunized animals and fused with a myeloma cell line to obtain a hybridoma. Then, an anti-MSLN antibody with high binding affinity was obtained by screening.

Murine anti-MSLN monoclonal antibodies were humanized by transplantation of light or heavy chain CDRs into human IgG1 or heavy chain framework regions. The CDRs of the murine anti-MSLN antibody light and heavy chains were determined using Kabat system. By aligning the antibody variable region database, we identified a human IgG1 framework region with high homology to the murine MSLN antibody. Thus, we designed different light chain variable region sequences of humanized MSLN antibody and different heavy chain variable region sequences of humanized anti-MSLN. According to this design, we synthesized variable region sequences of the humanized heavy and light chains, and fused the humanized MSLN antibody light chain variable region with the human kappa constant region by PCR, so as to obtain the humanized MSLN light chain in full length; and we fused the humanized MSLN heavy chain variable region with the IgG constant region by PCR to obtain the humanized MSLN heavy chain in full length. The different light and heavy chains were combined and expressed, and the purified humanized antibodies were compared with the human-murine chimeric antibody in term of ELISA binding affinity, and a candidate humanized antibody (designated as RC88 antibody) was obtained by screening.

Table 3 below shows the CDR amino acid sequences of the RC88 antibody light and heavy chains.

TABLE 3

Amino acid sequences of heavy and light chains of RC88 antibody

| Heavy chain | CDR1 SEQ ID NO: 1 | Gly Phe Asp Phe Ser Arg Tyr Trp Met Ser |
| | CDR2 SEQ ID NO: 2 | Glu Ile Asn Pro Asp Ser Ser Thr Ile Val Tyr Thr Pro Ser Leu Lys Asp |
| | CDR3 SEQ ID NO: 3 | Arg Gly Ser His Tyr Tyr Gly Tyr Arg Thr Gly Tyr Phe Asp |
| Light chain | CDR1 SEQ ID NO: 4 | Ser Ala Ser Ser Ser Val Ser Tyr Met Tyr |
| | CDR2 SEQ ID NO: 5 | Asp Thr Ser Asn Leu Ala Ser |
| | CDR3 SEQ ID NO: 6 | Gln Gln Trp Ser Ser Tyr Pro Pro Thr |

The amino acid sequence of RC88 antibody heavy chain variable region (SEQ ID NO:7):

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asp Phe Ser Arg Tyr
            20                  25                  30
Trp Met Ser Trp Val Arg Gln Ala Pro Gly Lys Gly Leu Glu Trp Ile
        35                  40                  45
Gly Glu Ile Asn Pro Asp Ser Ser Thr Ile Val Tyr Thr Pro Ser Leu
    50                  55                  60
Lys Asp Lys Phe Ile Ile Ser Arg Asp Asn Ala Lys Asn Thr Leu Tyr
65                  70                  75                  80
Leu Gln Met Asn Ser Leu Arg Ala Glu Asp Thr Ala Leu Tyr Tyr Cys
                85                  90                  95
Ala Arg Arg Gly Ser His Tyr Tyr Gly Tyr Arg Thr Gly Tyr Phe Asp
                100                 105                 110
Val Trp Gly Ala Gly Thr Thr Val Thr Val Ser Ser
            115                 120
```

The amino acid sequence of RC88 antibody light chain variable region (SEQ ID NO:8):

```
Asp Val Val Met Thr Gln Ser Pro Ala Phe Leu Ser Val Thr Pro Gly
  1               5                  10                 15
Glu Lys Val Thr Met Thr Cys Ser Ala Ser Ser Val Ser Tyr Met
            20                  25                  30
Tyr Trp His Gln Gln Lys Pro Asp Gln Ala Pro Lys Leu Leu Ile Tyr
            35                  40                  45
Asp Thr Ser Asn Leu Ala Ser Gly Val Pro Val Arg Phe Ser Gly Ser
        50                  55                  60
Gly Ser Gly Thr Asp Phe Thr Phe Thr Ile Ser Arg Met Glu Ala Glu
 65                 70                  75                  80
Asp Ala Ala Thr Tyr Tyr Cys Gln Gln Trp Ser Ser Tyr Pro Pro Thr
                85                  90                  95
Phe Gly Gly Gly Thr Lys Val Glu Ile Lys
            100                 105
```

The amino acid sequences of RC88 antibody light and heavy chains are set froth in Sequence 9 (SEQ ID NO:9) and Sequence 10 (SEQ ID NO:10).

Example 2: Preparation of Antibody Drug Conjugate (ADC)

Example 2a: Preparation of Linker-Drug Conjugate

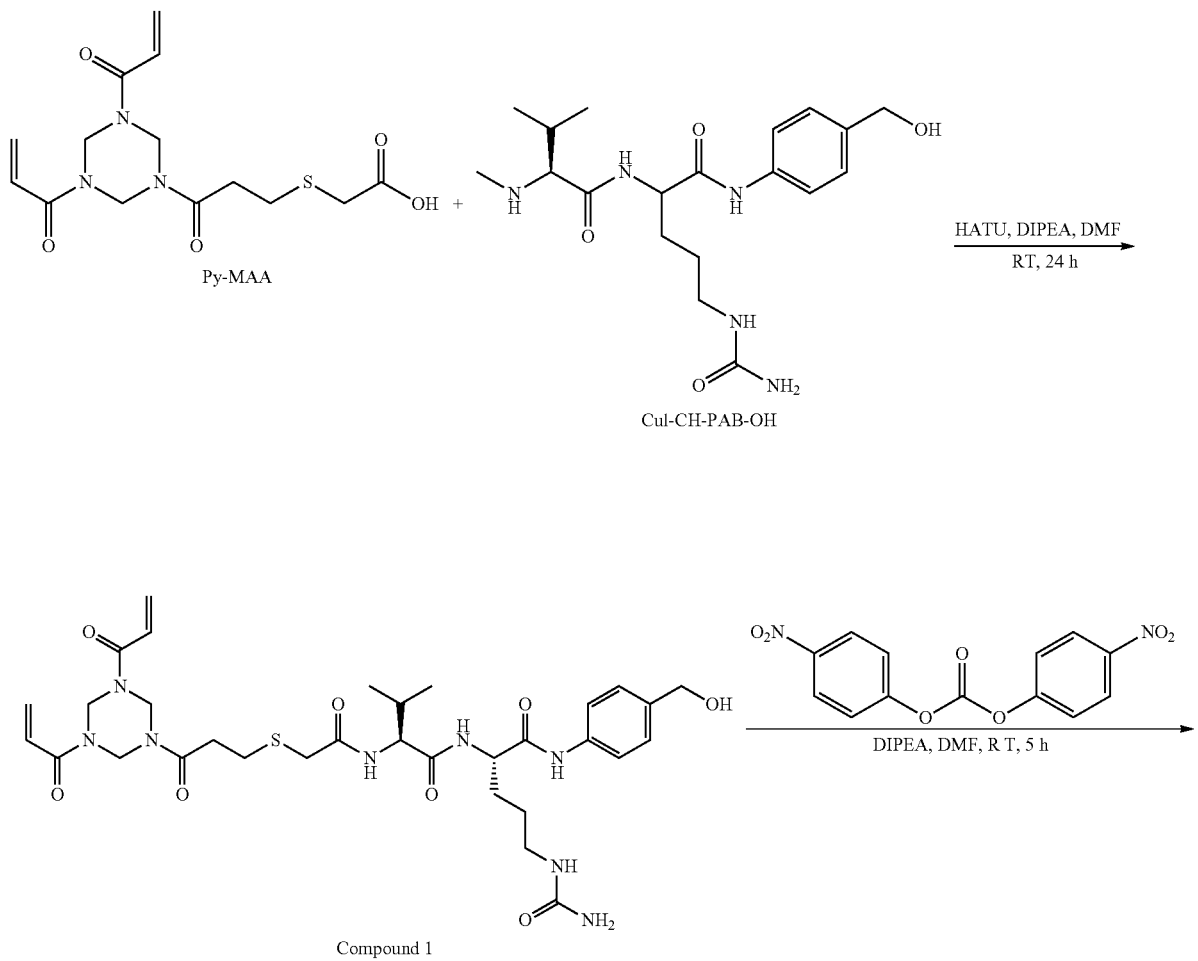

Compound 1

-continued
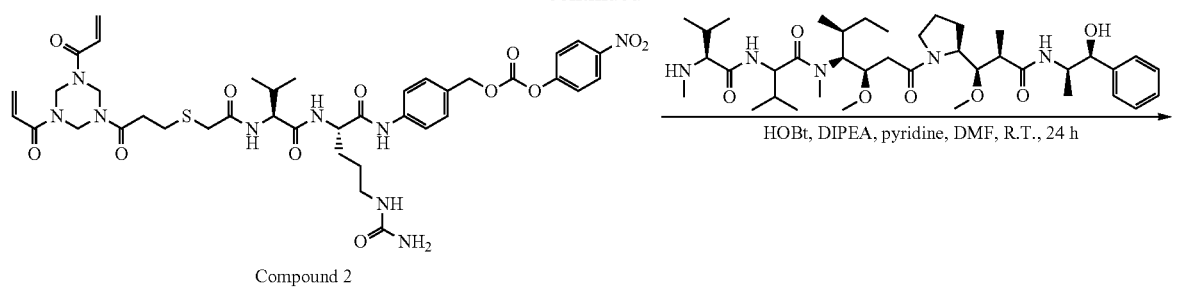
Compound 2
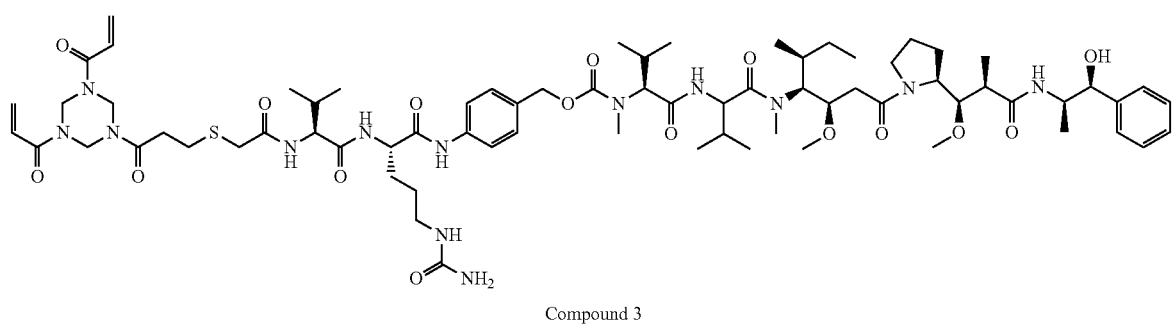
Compound 3
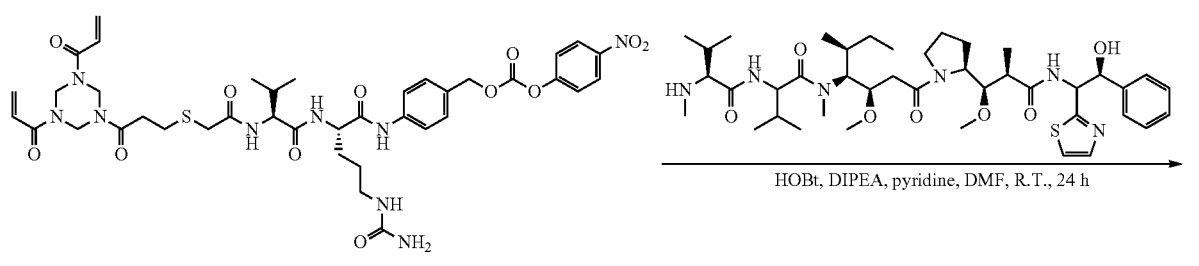
Compound 2
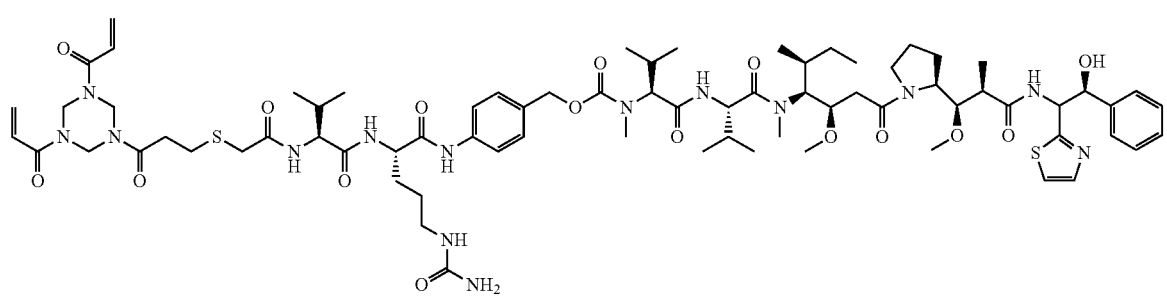
Compound 4
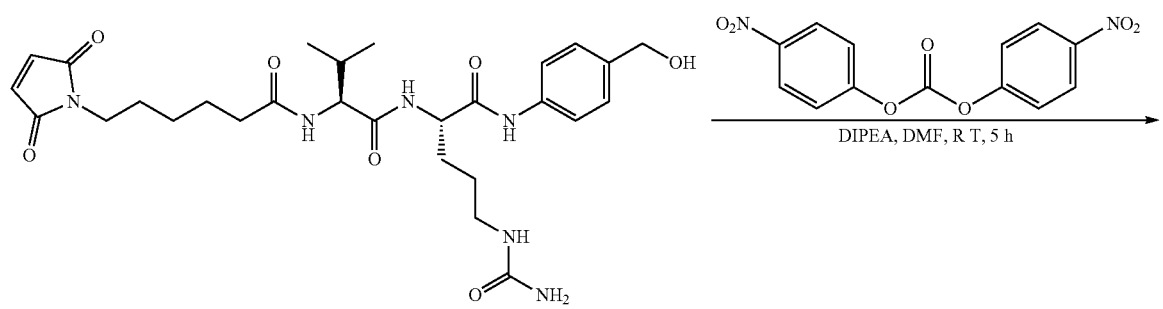
Compound 5

-continued

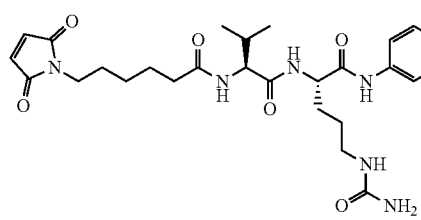

Compound 6

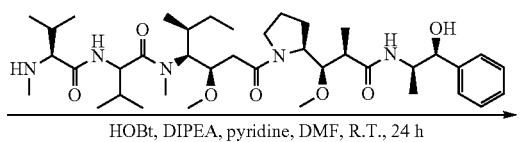

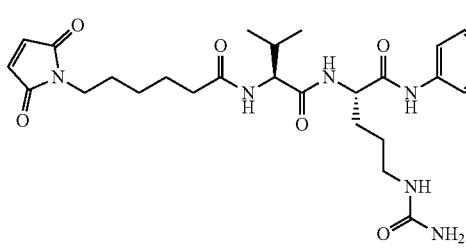

Compound 7

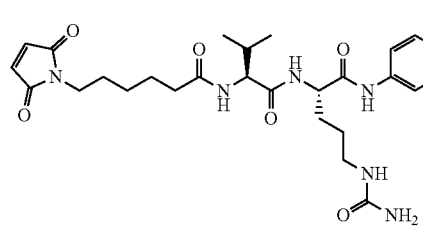

Compound 6

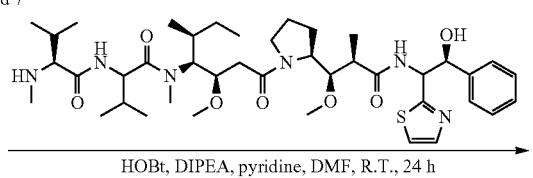

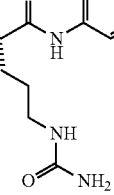

Compound 8

(1) Synthesis of Compound 1
(Py-MAA-Val-Cit-PAB-OH)

The compound Py-MAA (1,3,5-triacryloylhexahydro-1,3,5-triazine-mercaptoacetic acid, 10.00 g, 29.3 mmol) was dissolved in DMF (200 mL), added with HATU (16.73 g, 44.0 mmol), Val-Cit-PAB-OH (9.20 g, 23.4 mmol), DIPEA (15.32 ml,87.9 mmol), and stirred at room temperature for 24 hours, and the reaction progress was monitored by TLC. After the reaction was completed, the solvent was rotary evaporated under reduced pressure, and the crude product was purified by preparative high-performance liquid chromatography, and the resultant solution was rotary evaporated under reduced pressure to give Compound 1 (6.67 g, 32.4%, white solid powder).

(2) Synthesis of Compound 2
(Py-MAA-Val-Cit-PAB-PNP)

Compound 1 (7.02 g, 10.0 mmol) was dissolved in DMF (200 mL), and added with NPC (di(p-nitrophenyl) carbonate, 4.56 g, 15.0 mmol) and DIPEA (2.09 mL, 12 mmol); the reaction was carried out for 5 hours at room temperature, and the reaction progress was monitored by TLC. After the reaction was completed, the reaction mixture was poured into petroleum ether (1500 mL), stirred, filtered, and the obtained filter cake was washed with petroleum ether (150 mL×3) and dried by suction to give off-white solid powder (6.57 g, 75.7%).

(3) Synthesis of Compound 3 (Py-MAA-Val-Cit-PAB-MMAE)

Compound 2 (1.74 g, 2.2 mmol) was dissolved in 20 mL of DMF, and added with MMAE (1.44 g, 2.0 mmol), HOBt (0.27 g, 2.0 mmol), DIPEA (0.70 mL, 4.0 mmol) and pyridine (4 mL) under the protection of nitrogen gas. Under stirring at room temperature for 24 hours, the reaction progress was monitored by TLC. After the reaction was completed, purification was carried out by preparative high-performance chromatography, and the resultant solution was rotary evaporated under reduced pressure to give Compound 3 (white solid powder, 1.35 g, 46.7%). LC-MS m/z (ES+), 1446.35 (M+H)+, IR (3334.32 cm−1, 2965.9 cm−1, 1652.70 cm−1, 1538.92 cm−1, 1436.71 cm−1).

(4) Synthesis of Compound 4 (Py-MAA-Val-Cit-PAB-MMAD)

Compound 2 (0.87 g. 1.1 mmol) was dissolved in 10 mL of DMF, and added with MMAD (0.77 g, 1.0 mmol), HOBt (0.14 g. 1.0 mmol), DIPEA (0.35 mL, 2.0 mmol) and pyridine (2 mL) under the protection of nitrogen gas. Under stirring at room temperature for 24 hours, the reaction progress was monitored by TLC. After the reaction was completed, purification was carried out by preparative high-performance chromatography, and the resultant solution was rotary evaporated under reduced pressure to give Compound 4 (white solid powder, 0.65 g, 43.5%). LC-MS m/z (ES+), 1499.76 (M+H)+.

(5) Synthesis of Compound 6 (Mc-Val-Cit-PAB-PNP)

Compound 5 (Mc-Val-Cit-PAB, 4.58 g. 8.0 mmol) was dissolved in DMF (100 mL), added with NPC (di(p-nitrophenyl) carbonate, 3.65 g, 12.0 mmol) and DIPEA (1.70 mL, 9.6 mmol), reacted for 5 hours at room temperature, and the reaction progress was monitored by TLC. After the reaction was completed, the reaction mixture was poured into petroleum ether (1000 mL), stirred and filtered, and the obtained filter cake was washed with petroleum ether (60 mL×3) and dried by suction to give a off-white solid powder (5.04 g, 85.2%).

(6) Synthesis of Compound 7 (Mc-Val-Cit-PAB-MMAE)

Compound 6 (1.19 g. 1.6 mmol) was dissolved in 12 mL of DMF, and added with MMAE (1.08 g, 1.5 mmol), HOBt (0.21 g, 1.5 mmol), DIPEA (0.55 mL, 3.0 mmol) and pyridine (2.5 mL) under the protection of nitrogen gas. Under stirring at room temperature for 24 hours, the reaction progress was monitored by TLC. After the reaction was completed, purification was carried out by preparative high-performance chromatography, and the resultant solution was rotary evaporated under reduced pressure to give Compound 7 (white solid powder, 0.891 g, 45.1%). LC-MS m/z (ES+), 1316.18 (M+H)+.

(7) Synthesis of Compound 8 (Mc-Val-Cit-PAB-MMAD)

Compound 6 (0.74 g. 1.1 mmol) was dissolved in 10 mL of DMF, and added with MMAD (0.77 g. 1.0 mmol), HOBt (0.14 g. 1.0 mmol), DIPEA (0.35 mL, 2.0 mmol) and pyridine (2 mL) under the protection of nitrogen gas. Under stirring at room temperature for 24 hours, the reaction progress was monitored by TLC. After the reaction was completed, purification was carried out by preparative high-performance chromatography, and the resultant solution was rotary evaporated under reduced pressure to give Compound 8 (white solid powder, 0.59 g, 42.8%). LC-MS m/z (ES+), 1369.38 (M+H)+.

Example 2b: Preparation of Antibody Drug Conjugates

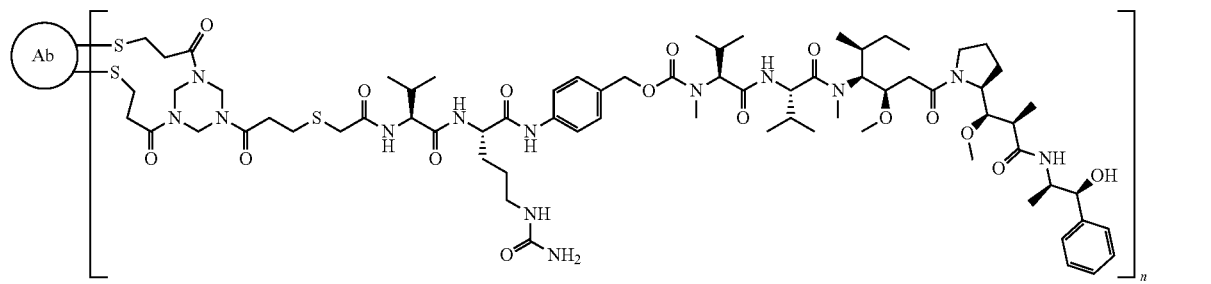

RC88-PY-MAA-Val-Cit-PAB-MMAE

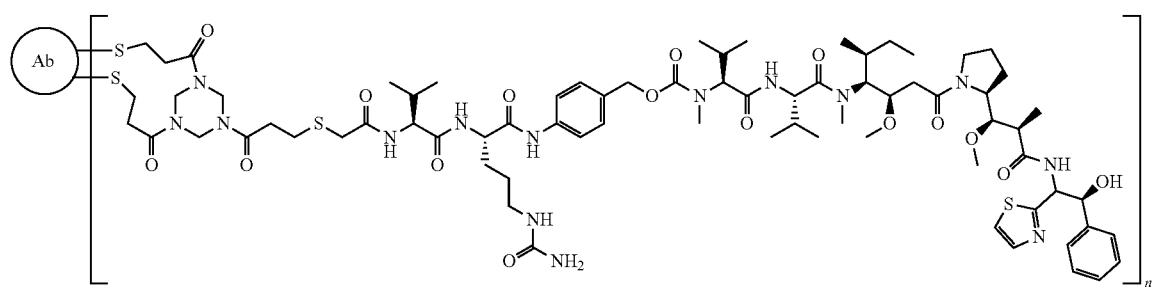

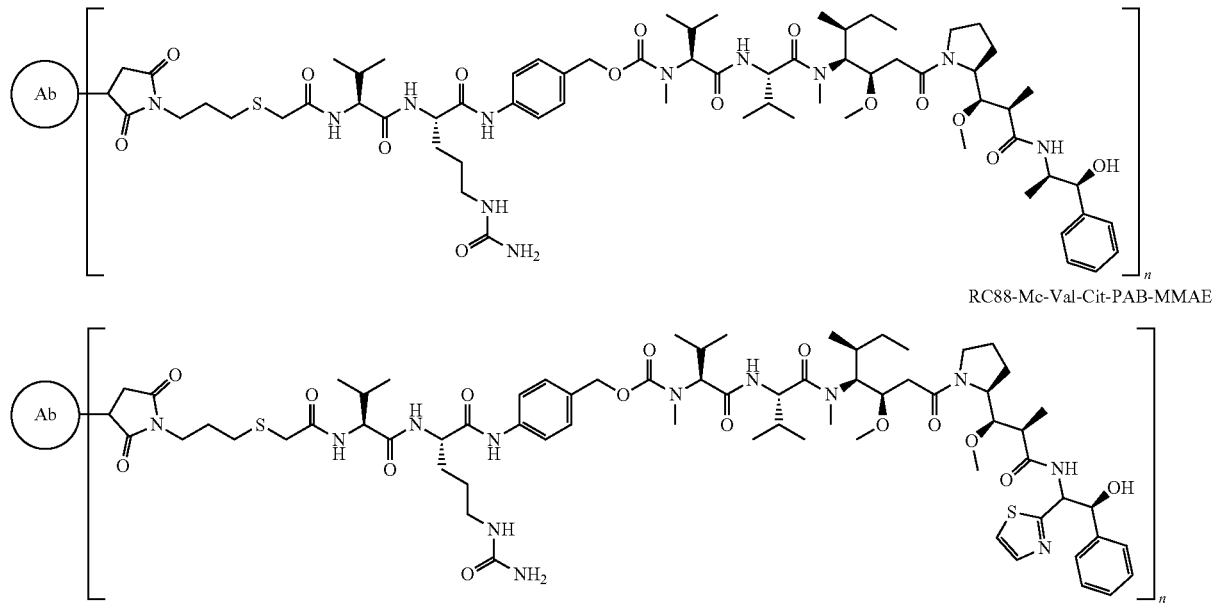

Figure 2:
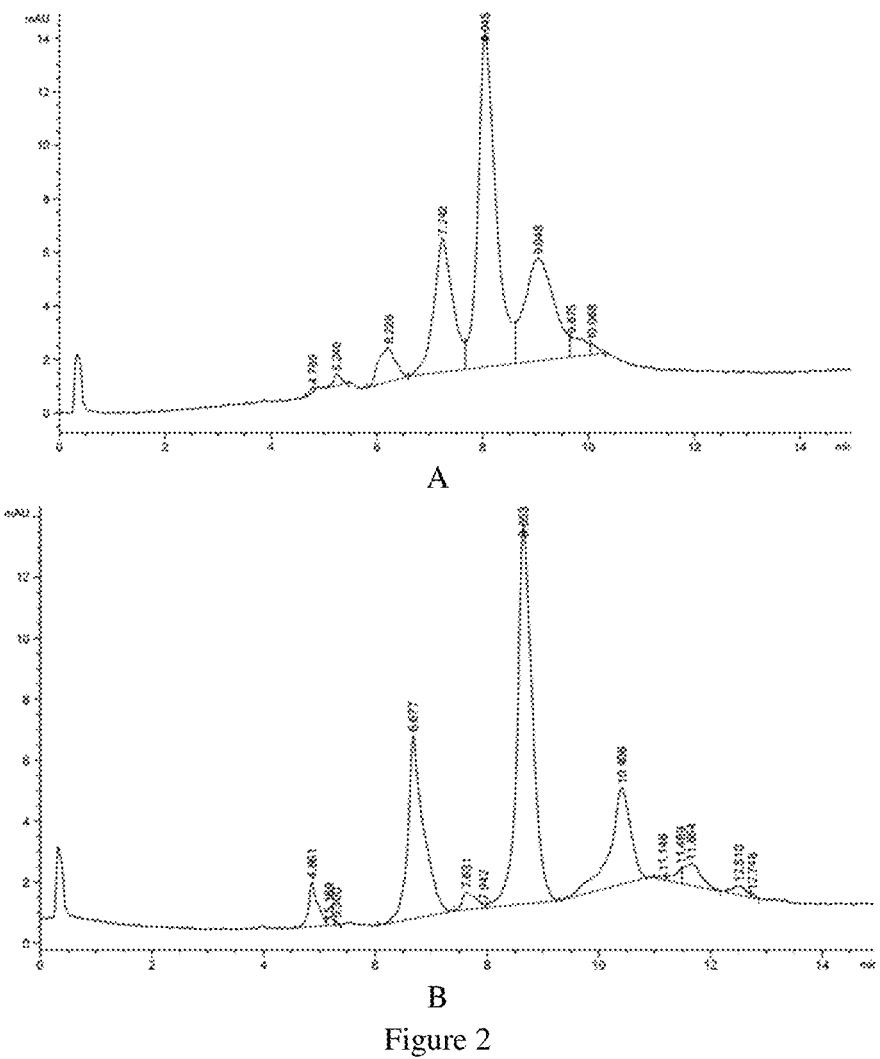
FIG. 2 shows the coupling of the conjugates of the present invention, wherein Figure A shows the detection results of the coupling of RC88-PY-MAA-Val-Cit-PAB-MMAE by hydrophobic high performance liquid chromatography (HIC-HPLC); Figure B shows the detection results of the coupling of RC88-Mc-Val-Cit-PAB-MMAE by hydrophobic high performance liquid chromatography (HIC-HPLC).

RC88-Mc-Val-Cit-PAB-MMAD 10 mg/mL RC88 antibody, 10 mmol/L DTPA (diethylene triamine pentacetate acid) and 5 molar-folds of 5 mmol/L TCEP (tris-2-carboxyethyl-phospine) were added to a PCR tube, stirred at 25° C. for 2 hours, then added at 0° C. with 25% DMSO (dimethyl sulfoxide) and 5 molar-folds of 5 mmol/L drug (Compound 3, 4, 7 or 8), stirred at 25° C. for 10 hours. After the reaction was completed, ultrafiltration was performed by centrifugation by PBS buffer for 3 times to purify and remove residual unreacted drug and free small molecules such as DMSO, and the coupling was detected by SDS-PAGE electrophoresis and hydrophobic high performance liquid chromatography (HIC-HPLC). RC88-PY-MAA-Val-Cit-PAB-MMAE and RC88-Mc-Val-Cit-PAB-MMAE were characterized by reduction SDS-PAGE, and this experiment used Novex's NuPAGE pre-made glue, and the total sample volume for each sample was 10 μL, and the results were shown in FIG. 1. For RC88-PY-MAA-Val-Cit-PAB-MMAE, since its bridged-linker links the reduced disulfide bonds with covalent bonds again, there were different bands, in which 150 kDa was intact antibody (LHHL), 125 kDa represented that one light chain was not coupled (LHH), 100 kDa was that two heavy chains were coupled (HH), 75 kDa was that one light chain and one heavy chain were coupled (LH), 50 kDa and 25 kDa were heavy and light chains, respectively. For RC88-Mc-Val-Cit-PAB-MMAE, there was not a bridged-linker, the disulfide bond was reduced into two sulfhydryl groups and then coupled to two linker-toxins respectively, so that the reduced SDS-PAGE showed only two bands of 50 kDa and 25 kDa. The coupling of RC88-PY-MAA-Val-Cit-PAB-MMAE and RC88-Mc-Val-Cit-PAB-MMAE was detected by hydrophobic high performance liquid chromatography (HIC-HPLC), the results were shown in FIG. 2A and FIG. 2B, and the results showed that the DAR values were 3.95 (RC88-PY-MAA-Val-Cit-PAB-MMAE) and 3.9 (RC88-Mc-Val-Cit-PAB-MMAE), respectively.

Example 3: Construction of Oval-Citar-3 Cells with High Expression of MSLN

Oval-Citar-3 cells (ATCC) in good growth were inoculated into 6-well plates at $3 \times 10^5$/well; after adhering overnight, the original medium was discarded and 400 μL of fresh medium containing 10 μg/mL Polybrene (sigma) was added, and 600 μL of lentiviral vector (pRRL-cmv) containing human MSLN coding sequence at a suitable concentration was added at the meantime; after mixing well, the culture was continued for 24 hours. After the end of the culture, replacement with fresh medium was performed and expanding culture was carried out, and the positive cells were selected using a flow cytometer. The selected positive cells were used for expanding culture, the expression of MSLN was analyzed by flow cytometer, and the cells with the highest expression of MSLN (hereinafter referred to as Oval-Citar-3-MSLN) were selected for subsequent experiments.

Figure 3:
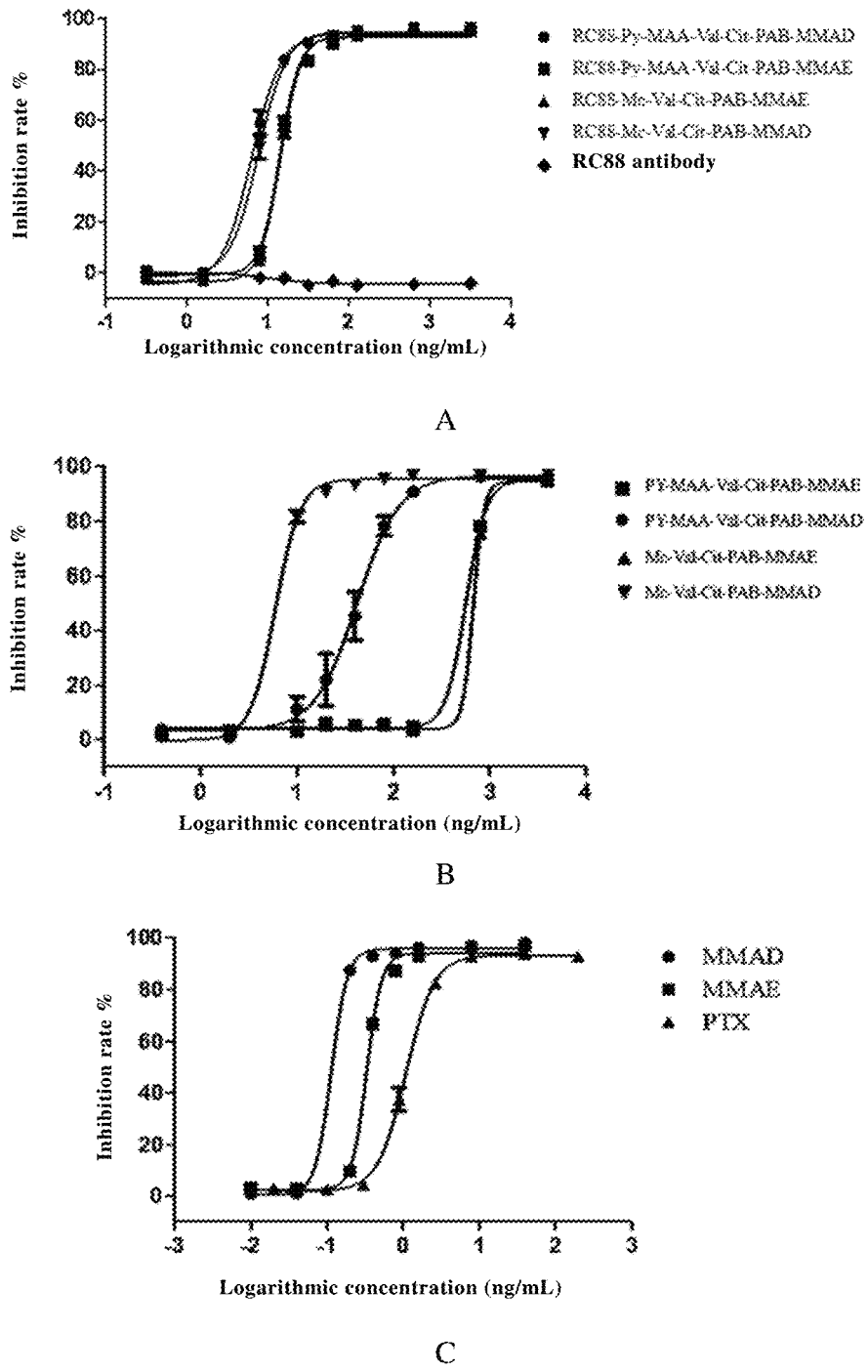
FIG. 3 shows the cytotoxic effects of the conjugates of the present invention, wherein Figure A shows the cytotoxic effect curves of the RC88 antibody drug conjugates of the present invention (i.e., RC88-Py-MAA-Val-Cit-PAB-MMAE, RC88-Py-MAA-Val-Cit-PAB-MMAD, RC88-Mc-Val-Cit-PAB-MMAE, RC88-Mc-Val-Cit-PAB-MMAD) in Oval-Citar-3 cells with high expression of MSLN; Figure B shows the cytotoxic effect curves of the unconjugated antibody linkers and the cytotoxin-conjugates (Py-Val-Cit-PAB-MMAE, Py-Val-Cit-PAB-MMAD, Mc-Val-Cit-PAB-MMAE, Mc-Val-Cit-PAB-MMAD) in Oval-Citar-3 cells with high expression of MSLN; Figure C shows the cytotoxic effect curves of cytotoxin MMAE, MMAD and positive control PTX (Paclitaxel) in Oval-Citar-3 cells with high expression of MSLN; wherein the abscissa represents the logarithmic concentration of drug and the ordinate represents the maximum inhibition rate at the corresponding logarithmic concentration of drug.

Example 4: Detection of Cytotoxic Activity of RC88 Antibody and RC88 Antibody Drug Conjugate and Corresponding Linker-Drug and Drug Oval-Citar-3-MSLN cells in good growth state were added to a 96-well cell culture plates ($5 \times 10^4$ cells/mL. 100 μL/well), and incubated overnight at 37° C. in a $CO_2$ incubator. RC88 antibody, RC88 antibody drug conjugates (RC88-Py-MAA-Val-Cit-PAB-MMAE, RC88-Py-MAA-Val-Cit-PAB-MMAD, RC88-Mc-Val-Cit-PAB-MMAE, RC88-Mc-Val-Cit-PAB-MMAD) and the corresponding linker-drug conjugates (Py-Val-Cit-PAB-MMAE, Py-Val-Cit-PAB-MMAD, Mc-Val-Cit-PAB-MMAE, Mc-Val-Cit-PAB-MMAD), drugs (MMAE, MMAD), PTX (Paclitaxel) were diluted with complete medium at the following concentrations: for RC88 antibody, RC88 antibody drug conjugates (RC88-Py-MAA-Val-Cit-PAB-MMAE, RC88-Py-MAA-Val-Cit-PAB-MMAD, RC88-Mc-Val-Cit-PAB- MMAE, RC88-Mc-Val-Cit-PAB-MMAD), the final concentrations were: 0.32, 1.6, 8, 16, 32, 64, 128, 640, 3200 ng/ml; for the linker-drug conjugates (Py-Val-Cit-PAB-MMAE, Py-Val-Cit-PAB-MMAD, Mc-Val-Cit-PAB-MMAE, Mc-Val-Cit-PAB-MMAD), the final concentrations were: 0.4, 2, 10, 20, 40, 80, 160, 800, 4000 ng/ml; for the drugs (MMAE, MMAD), the final concentrations were: 0.0016, 0.008, 0.04, 0.2, 0.4, 0.8, 1.6, 8, 40 ng/mL; for the PTX (Paclitaxel), the final concentrations were: 0.004, 0.02, 0.098, 0.3, 0.89, 2.67, 8, 40, 200 ng/mL. After dilution, they were added to 96 plates (100 μL/well), and a blank group (equal volume of medium without drug) and three control groups were set, and incubation was carried out in a $CO_2$ constant temperature incubator at 37° C. for 72 hours. A medium (without FBS) that contained 10 μL of CCK-8 at a dose of 100 μL/well was added, incubated at 37° C. for 2 to 4 hours in a $CO_2$ incubator, and the OD values at 450 nm were read with a microplate reader. The inhibition rate was calculated by the following formula: IR %=($OD_{blank}$−$OD_{drug}$)×100/$OD_{blank}$. Using Prism software, the inhibition rate was taken as y value, the drug concentration was used as x value, and four-parameter curve fitting was performed; and the drug concentration value corresponding to the value between the maximum inhibition rate and the minimum inhibition rate was recorded ($IC_{50}$ value was defaulted by the software), and the results were shown in FIG. 3 and Table 4. The results showed that RC88-Py-MAA-Val-Cit-PAB-MMAD, RC88-Mc-Val-Cit-PAB-MMAD, RC88-Py-MAA-Val-Cit-PAB-MMAE, RC88-Mc-Val-Cit-PAB-MMAE were effective in inhibiting the growth of Oval-Citar-3-MSLN.

TABLE 4

Results of cytotoxicity IC50 values, maximum inhibition rates for RC88 antibody, RC88 antibody drug conjugates, corresponding linker-drug conjugates and drugs (N = 3)

| Samples | OVal-CitAR3-MSLN | | |
|---|---|---|---|
| | ng/ml | nM | Inhibition rate, % |
| RC88-Py-MAA-Val-Cit-PAB-MMAD | 6.5 ± 1.6 | 0.043 ± 0.011 | 95.6 ± 1.9 |
| RC88-Py-MAA-Val-Cit-PAB-MMAE | 14.1 ± 1.4 | 0.093 ± 0.009 | 95.0 ± 2.0 |
| RC88-Mc-Val-Cit-PAB-MMAE | 14.5 ± 1.5 | 0.0956 ± 0.010 | 95.8 ± 1.0 |
| RC88-Mc-Val-Cit-PAB-MMAD | 7.8 ± 1.7 | 0.0158 ± 0.011 | 96.2 ± 0.9 |
| RC88 antibody | — | — | −4.2 ± 1.2 |
| Py-MAA-Val-Cit-PAB-MMAD | 40.9 ± 22.9 | 27.30 ± 15.27 | 95.7 ± 0.6 |
| Py-MAA-Val-Cit-PAB-MMAE | ~684.6 | — | 94.9 ± 0.8 |
| Mc-Val-Cit-PAB-MMAE | ~663.4 | — | 94.5 ± 0.8 |
| Mc-Val-Cit-PAB-MMAD | 5.6 ± 0.03 | 4.39 ± 0.0179 | 96.9 ± 0.6 |
| MMAD | 0.1169 ± 0.0074 | 0.1517 ± 0.010 | 98.1 ± 2.4 |
| MMAE | 0.3199 ± 0.0284 | 0.4458 ± 0.0395 | 96.9 ± 0.7 |
| PTX | 1.087 ± 0.2623 | 1.27 ± 0.31 | 92.8 ± 1.5 |

Figure 4:
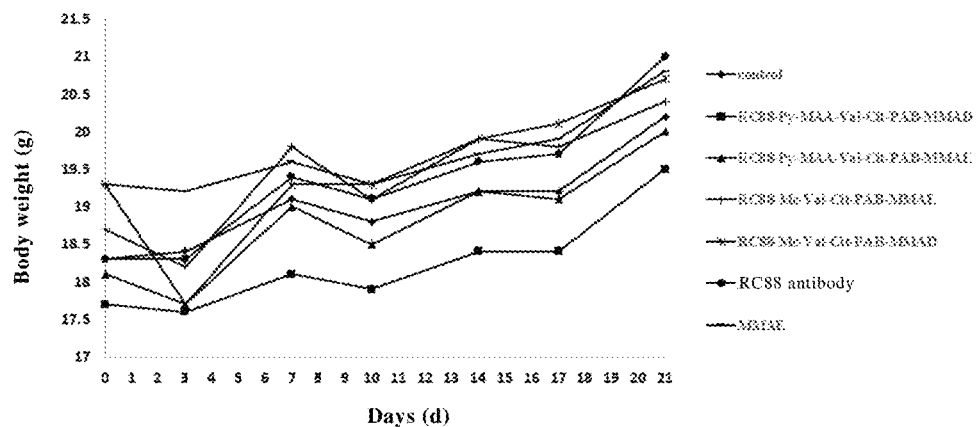
FIG. 4 shows the graph of the body weight of the tumor-bearing mice as a function of the number of days, wherein the mice were administrated with RC88 antibody (2 mg/kg), RC88 antibody drug conjugates (RC88-Py-MAA-Val-Cit-PAB-MMAD, RC88-Py-MAA-Val-Cit-PAB-MMAE, RC88-Mc-Val-Cit-PAB-MMAE, RC88-Mc-Val-Cit-PAB-MMAD, 2 mg/kg) and MMAE (0.0716 mg/kg) (administered once per week, 3 doses in total), wherein the abscissa represents the number of days, and the ordinate represents the body weight of the tumor-bearing mice after the corresponding days of administration. In this test, the control groups were saline (control) and MMAE.
Figure 5:
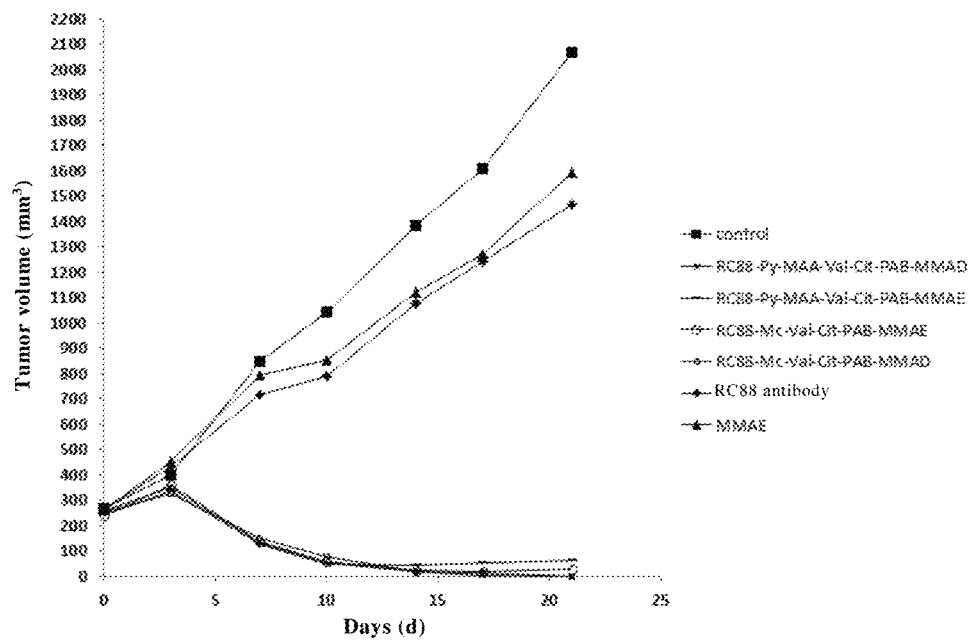
FIG. 5 shows the graph of the tumor volume of the tumor-bearing mice as a function of the number of days, wherein the mice were administrated with RC88 antibody (2 mg/kg), RC88 antibody drug conjugates (RC88-Py-MAA-Val-Cit-PAB-MMAD, RC88-Py-MAA-Val-Cit-PAB-MMAE, RC88-Mc-Val-Cit-PAB-MMAE, RC88-Mc-Val-Cit-PAB-MMAD, 2 mg/kg) and MMAE (0.0716 mg/kg) (administered once per week, 3 doses in total), wherein the abscissa represents the number of days, and the ordinate represents the tumor volume of the tumor-bearing mice after the corresponding number of days of administration. In this test, the control groups were saline (control) and MMAE.
Figure 6:
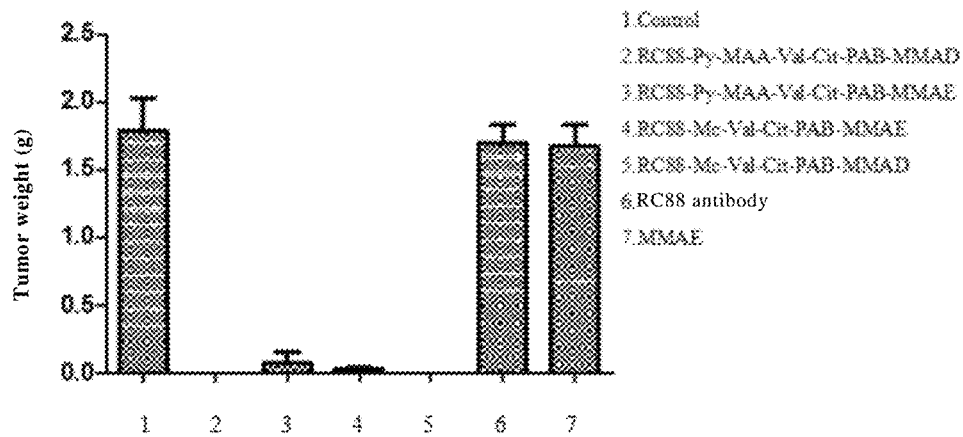
FIG. 6 shows the graph of the tumor weight of the tumor-bearing mice administrated with RC88 antibody (2 mg/kg), RC88 antibody drug conjugates (RC88-Py-MAA-Val-Cit-PAB-MMAD, RC88-Py-MAA-Val-Cit-PAB-MMAE, RC88-Mc-Val-Cit-PAB-MMAE, RC88-Mc-Val-Cit-PAB-MMAD, 2 mg/kg) and MMAE (0.0716 mg/kg), once per week for 3 times in total, the control groups were saline (control) and MMAE.

Example 5: Anti-Tumor Experiment of RC88 Antibody and RC88 Antibody Drug Conjugates in Oval-Citar-3 Human Ovarian Cancerbearing Mouse Model with High Expression of MSLN Oval-Citar-3-MSLN cells (2×10$^6$) in good growth state were subcutaneously inoculated into nude mice (Changzhou Cavans Laboratory Animal Co., Ltd., certificate number: 201611240, license number: SCXK (Su) 2011-0003), and the animals were randomized after the tumor volume grew to approximately 100-400 mm$^3$. RC88 antibody (2 mg/kg), RC88 antibody drug conjugates (RC88-Py-MAA-Val-Cit-PAB-MMAD, RC88-Py-MAA-Val-Cit-PAB-MMAD, RC88-Mc-Val-Cit-PAB-MMAE, RC88-Mc-Val-Cit-PAB-MMAD, 2 mg/kg) and MMAE (0.0716 mg/kg) were administrated, respectively, once a week, 3 times in total, and the negative control group was administrated with the equal volume of physiological saline at the same time. The results were shown in FIGS. 4, 5 and 6.

The results showed that RC88 antibody and RC88 antibody drug conjugates did not affect the body weight gain of the tumor-bearing mice; the RC88 antibody drug conjugates (RC88-Py-MAA-Val-Cit-PAB-MMAD, RC88-Py-MAA-Val-Cit-PAB-MMAE, RC88-Mc-Val-Cit-PAB-MMAE, RC88-Mc-Val-Cit-PAB-MMAD, 2 mg/kg) all showed significant inhibition of xenograft in the tumor-bearing mice, while RC88 antibody did not show significant anti-tumor effect.

Figure 7:
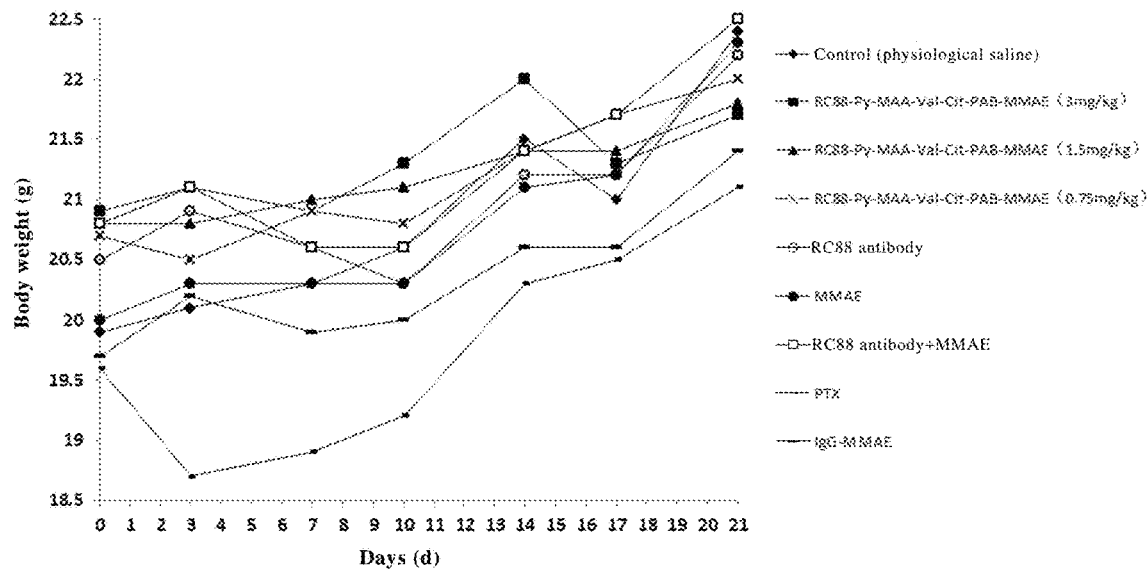
FIG. 7 shows the graph of the body weight of the tumor-bearing mice as a function of the number of days, wherein the mice were administrated with RC88 antibody (3 mg/kg), RC88 antibody drug conjugate (RC88-Py-MAA-Val-Cit-PAB-MMAE, 3 mg/kg, 1.5 mg/kg. 0.75 mg/kg), MMAE (0.06 mg/kg), RC88 antibody (3 mg/kg)+MMAE (0.06 mg/kg), IgG-MMAE (3 mg/kg), PTX (paclitaxel, 10 mg/kg) (PTX was administered twice per week, 6 times in total; others were administrated once per week, 3 times in total), wherein the abscissa represents the number of days, and the ordinate represents the body weight of the tumor-bearing mice after the corresponding number of days of administration. In this test, the control groups were saline (control) and MMAE.
Figure 8:
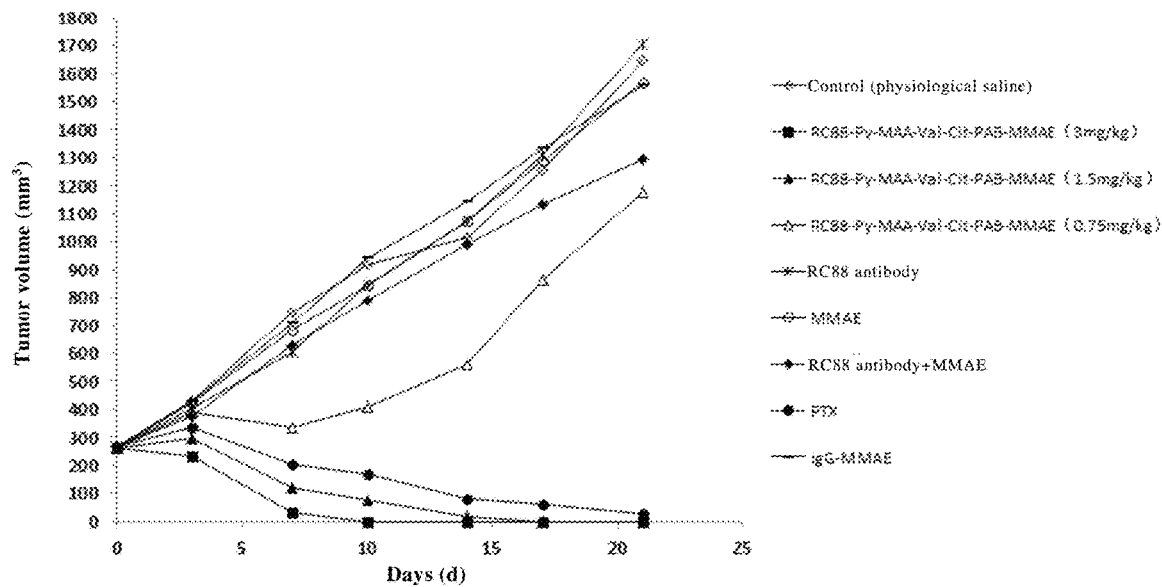
FIG. 8 shows the graph of the tumor volume of the tumor-bearing mice as a function of the number of days, wherein the mice were administrated with RC88 antibody (3 mg/kg), RC88 antibody drug conjugate (RC88-Py-MAA-Val-Cit-PAB-MMAE, 3 mg/kg, 1.5 mg/kg, 0.75 mg/kg), MMAE (0.06 mg/kg), RC88 antibody (3 mg/kg)+MMAE (0.06 mg/kg), IgG-MMAE (3 mg/kg), PTX (paclitaxel, 10 mg/kg) (administered once a week, a total of The tumor volume of the tumor-bearing mice with the drug 3 times (PTX was administered twice per week, 6 times in total; others were administrated once per week, 3 times in total), the abscissa represents the number of days, and the ordinate represents the tumor volume of the tumor-bearing mice after the corresponding number of days of administration. In this test, the control groups were saline (control) and MMAE.
Figure 9:
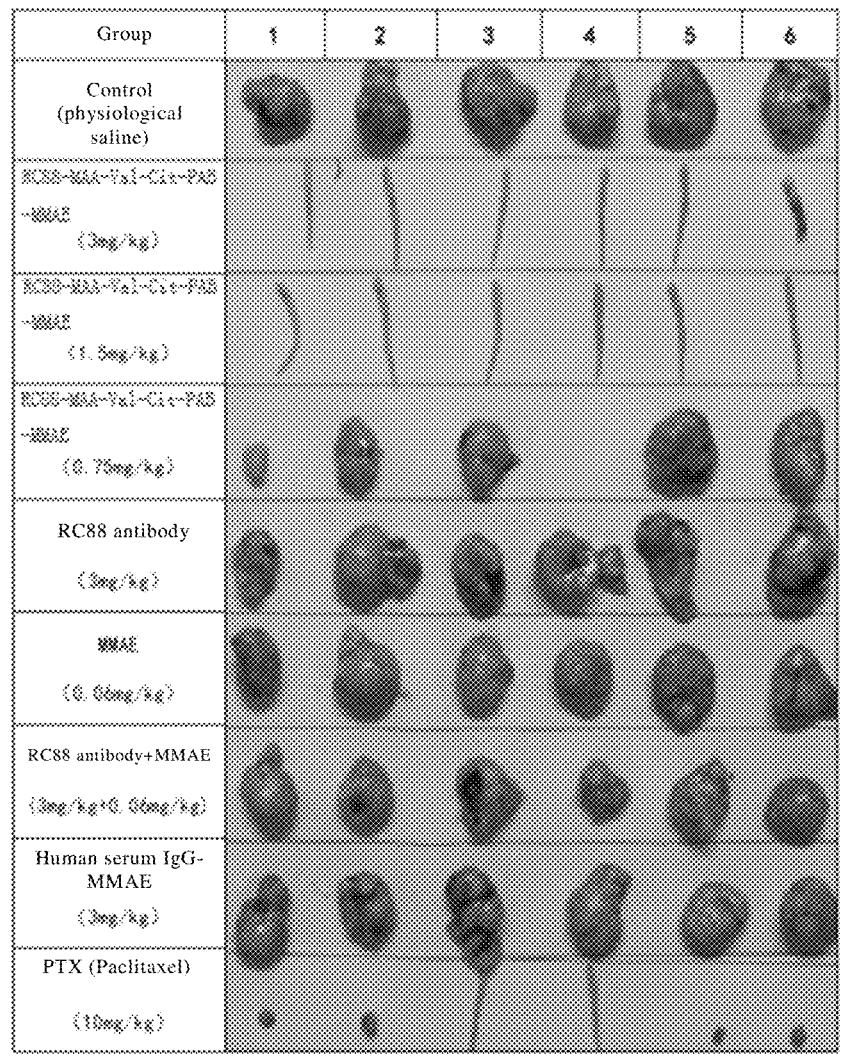
FIG. 9 shows the anti-tumor effects of the RC88 antibody drug conjugate (RC88-Py-MAA-Val-Cit-PAB-MMAE) in the Oval-Citar-3 human ovarian cancer-bearing mouse model with high expression of MSLN.

Example 6: Anti-Tumor Experiment of RC88 Antibody Drug Conjugates in Oval-Citar-3 Human Ovarian Cancer Bearing Mouse Model with High Expression of MSLN Oval-Citar-3-MSLN cells (2×10$^6$) in normal growth state were subcutaneously inoculated in nude mice (Changzhou Cavans Laboratory Animal Co., Ltd., certificate number: 201611240, license number: SCXK (Su) 2011-0003), and the animals were randomized after the tumor volume grew to approximately 100-400 mm$^3$. RC88 antibody (3 mg/kg), RC88 antibody drug conjugate (RC88-Py-MAA-Val-Cit-PAB-MMAE, 3 mg/kg, 1.5 mg/kg, 0.75 mg/kg), MMAE (0.06 mg/kg), RC88 antibody (3 mg/kg)+MMAE (0.06 mg/kg), human serum IgG-MMAE (3 mg/kg), PTX (Paclitaxel) (10 mg/kg) were administrated, respectively, once a week. 3 times in total (PTX was administered twice a week, 6 times in total), and the negative control group was administrated with the equal amount of physiological saline at the same time. The results were shown in FIGS. 7, 8, and 9. The results showed that for the RC88 antibody drug conjugate, the tumor-bearing mice in the 3 mg/kg group and the 1.5 mg/kg group showed a significant decrease of tumor after 7 days of the first administration, the 3 mg/kg group showed no visible tumor after 10 days of administration, the 1.5 mg/kg group showed no visible tumor after 17 days of administration, and the 0.75 mg/kg group showed that the tumor growth was still relatively fast after 3 times of administration, and there was no statistical difference in tumor volume after 21 days of administration in comparison with the control (saline) group (P>0.05) and T/C >40%. For the paclitaxel (PTX) group, after 21 days of administration, tumors were completely eliminated (CR) in two tumor-bearing mice, and tumor volume and RTV were statistically different from the control (saline) group (P<0.05), and T/C<40%. There was no statistical difference between the paclitaxel (PTX) group and the 3 mg/kg group and 1.5 mg/kg group of the RC88 antibody drug conjugate. There was no significant difference between the RC88 antibody group, the MMAE group, the RC88 antibody+MMAE group, the IgG-MMAE group and the control (saline) group (P>0.05).

Figure 10:
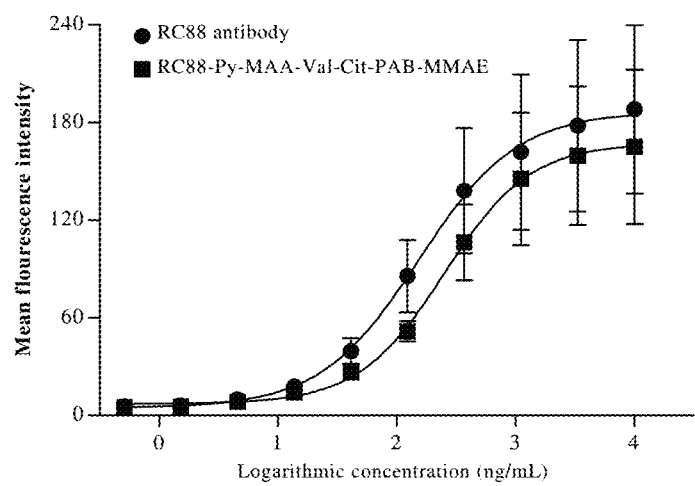
FIG. 10 shows the affinity curves of the RC88 antibody and the RC88 antibody drug conjugate (RC88-Py-MAA-Val-Cit-PAB-MMAE) versus MSLN positive tumor cells by ELISA assay.

Example 7: Detection of Affinity of RC88 Antibody and RC88 Antibody Drug Conjugate for MSLN Positive Tumor Cells Flow cytometer was used to detect the affinity of RC88 antibody and RC88 antibody drug conjugate (RC88-Py-MAA-Val-Cit-PAB-MMAE) for MSLN positive tumor cells. Logarithmic growth phase Oval-Citar-3-MSLN cells were centrifuged in 1.5 mL EP tubes ($4\times10^5$ per group) at 1500 rpm for 5 min and washed thoroughly with PBS, and the supernatant fraction was discarded; the cells were resuspended in paraformaldehyde (200 μL, 4%), fixed at 25° C. for 15 min, washed with PBS once, centrifuged at 2500 rpm for 3 min, and the supernatant fraction was discarded; the RC88 antibody and the RC88 antibody drug conjugate were diluted with cold 1% BSA-PBS (bovine serum albumin-PBS) buffer into 3-fold gradients from 10000 ng/mL to 1.52 ng/ml, and 200 μL of solution at each concentration was used to resuspend the cells. The cells of the blank control group were directly resuspended in cold 1% BSA-PBS, and the cells of the negative control group were resuspended in 5 μg/mL hIgG (Zhongke Chenyu) as prepared with 1% BSA. Incubation was performed at 4° C. for 30 min, and upside-down mixing was carried out once every 10 min for evenly incubating the cells; after the incubation, the cells were washed once with cold PBS, centrifuged at 2500 rpm for 3 min at 4° C., and the supernatant was discarded; 200 μL of FITC (Fluorescein Isothiocyanate)-labeled goat-anti-human IgG Fcγ (Jackson ImmunoResearch) 1:200 diluted with cold PBS was added to each tube, incubated at 4° C. for 30 min, and upside-down mixing was carried out once every 10 min for evenly incubating the cells. At the end of the incubation, the cells were washed once with cold PBS, centrifuged at 2500 rpm for 5 min at 4° C. the supernatant was discarded; the cells was resuspended in 400 μL of PBS, transferred to a flow cytometer (BD Calibur) for detection, and the results were shown in FIG. 10. The results showed that both the RC88 antibody and the RC88 antibody drug conjugate (RC88-Py-MAA-Val-Cit-PAB-MMAE) had strong binding affinity to MSLN positive tumor cells with EC50 values of 153.5 ng/ml and 251.4 ng/ml, respectively.

Figure 11:
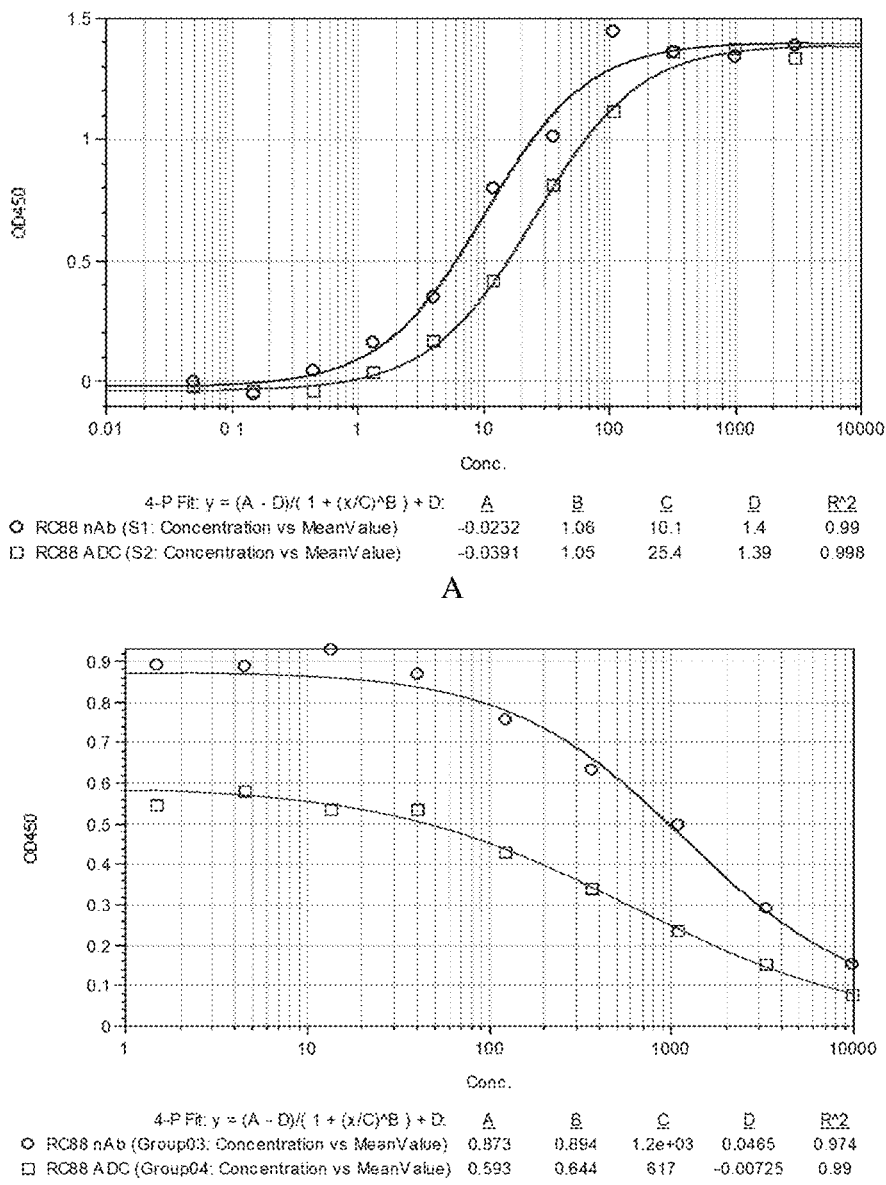
FIG. 11 shows the affinity of the conjugate of the present invention to the target, wherein Figure A shows the affinity curves of the RC88 antibody and the RC88 antibody drug conjugate (RC88-Py-MAA-Val-Cit-PAB-MMAE) versus MSLN positive tumor cells by ELISA assay; Figure B shows competitive binding curves of the RC88 antibody and the RC88 antibody drug conjugate (RC88-Py-MAA-Val-Cit-PAB-MMAE) versus the recombinant human MSLN protein.

Example 8: Detection of Binding Activity of RC88 Antibody and RC88 Antibody Drug Conjugate to MSLN Positive Tumor Cells The binding activity of the RC88 antibody and the RC88 antibody drug conjugate (RC88-Py-MAA-Val-Cit-PAB-MMAE) to MSLN positive tumor cells was detected by ELISA method. Logarithmic growth phase Oval-Citar-3-MSLN cells were added to 96-well cell culture plates ($4\times10^5$ cells/mL, 100 μL/well), incubated at 37° C. overnight in a $CO_2$ incubator, the supernatant fraction was discarded, and the plate was washed 3 times with 0.05% PBST buffer (250 μL/well); 100 μL of 4% paraformaldehyde was added per well, and fixed for 30 min at 25° C., and the plate was washed 3 times with 0.05% PBST buffer (250 μL/well); each well was added with 250 μL of 3% BAS-PBST (bovine serum albumin-PBST), and the plate was washed 3 times with 0.05% PBST buffer (250 μL/well) after incubating at room temperature for 2 hours; sample loading: 1) binding curve: the RC88 antibody and the RC88 antibody drug conjugate were diluted in 3-fold gradients from 3000 ng/ml to 0.05 ng/ml with 1% BAS-PBST buffer, and then added to a 96-well plate (100 μL/well); 2) competition curve: recombinant human MSLN protein (Yiqiao Shenzhou) was diluted from 10000 ng/ml to 0.51 ng/mL with 1% BAS-PBST, the RC88 antibody and the RC88 antibody drug conjugate were diluted to 20 ng/ml, then mixed with MSLN protein dilution in equal volume, and added to a 96-well plate in 100 μL/well; after incubation at 25° C. for 1 hour, the plate was washed 3 times; each well was added with 1% BAS-PBST diluted HRP (Horseradish Peroxidase)-labeled goat-anti-human IgG Fc (Bethyl) (1:2000), after incubation at 25° C. for 1 hour, the plate was washed 3 times; TMB color development kit (Kangwei Century) was used for development in dark for 5-10 min, 2M sulfuric acid was used for termination, the plate was read with a microplate reader, and the results were shown in the FIG. 11. The results showed that both of the RC88 antibody and the RC88 antibody drug conjugates were strongly bound to MSLN positive tumor cells; the RC88 antibody drug conjugate showed a slight decrease compared with the RC88 antibody, but there was no significant difference, and their $EC_{50}$ values were 11.0±0.81 ng/ml and 19.7±5.80 ng/ml, respectively. The competition experiment with recombinant human MSLN protein demonstrated that the RC88 antibody and the RC88 antibody drug conjugate were specifically bound to MSLN on surface of Oval-Citar-3-MSLN cells.

Figure 12:
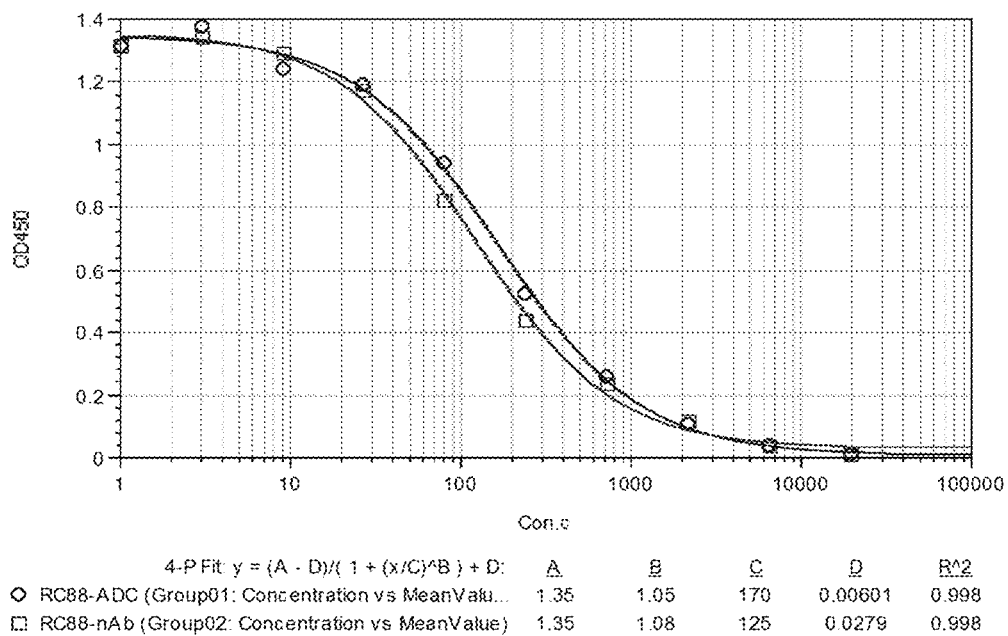
FIG. 12 shows the competitive binding curves of the RC88 antibody and the RC88 antibody drug conjugate (RC88-Py-MAA-Val-Cit-PAB-MMAE) and CA125 versus the recombinant human MSLN protein.

Example 9: Competitive Binding of RC88 Antibody and RC88 Antibody Drug Conjugate and CA125 to MSLN The competitive binding ability of the RC88 antibody and the RC88 antibody drug conjugate (RC88-Py-MAA-Val-Cit-PAB-MMAE) and CA125 to MSLN was determined by ELISA. ELISA plates were coated with recombinant protein MSLN (Yiqiao Shenzhou, 200 ng/ml). Sample loading: the RC88 antibody and the RC88 antibody drug conjugate were diluted with 1% BAS-PBST (bovine serum albumin-PBST) buffer to reach 10 points from 20 μg/mL (50 μL/well), the recombinant protein CA125 (his tag. R&D) was diluted with 1% BAS-PBST buffer to 200 ng/ml (50 μL/well); the total reaction system was 100 μL/well, secondary antibody (mouse-anti-his monoclonal antibody. R&D) was diluted by 5000 times, 100 μL/well, TMB (3,3',5,5'-tetramethylbenzidine) was used for color development for 5-7 min, then the reaction was terminated with 2M sulfuric acid, the plate was read at 450 nm with a microplate reader, and the results were shown in FIG. 12. The results showed that the binding of recombinant CA125 protein to recombinant human MSLN protein decreased with the concentration increase of the RC88 antibody and the RC88 antibody drug conjugate, indicating that the RC88 antibody and the RC88 antibody drug conjugate could block the binding of recombinant human CA125 protein to recombination human MSLN protein.

The above descriptions are intended to preferred embodiments, which are only examples and do not limit the combination of the features required to practice the invention. The headings provided are not meant to limit the various embodiments of the invention. Terms such as "including", "comprising" and "encompassing" are not intended to limiting. In addition, unless otherwise indicated, plural forms are included when there is not a numeral modificaiton, and the word "or" refers to "and/or". Unless otherwise defined herein, all technical and scientific terms used herein have the same meaning as commonly understood by those skilled in the art.

All publications and patents mentioned in this application are hereby incorporated by reference. Numerous modifications and variations of the described methods and compositions of the present invention will be apparent to those skilled in the art. While the invention has been described by way of specific preferred embodiments, it should be understood that the present invention should not be limited to these embodiments. In fact, many variations of the described modes for carrying out the invention that are obvious to those skilled in the art are intended to be included within the scope of the appended claims.

What is claimed is:

1. An antibody drug conjugate, which has the formula of Ab-(L-D)$_n$, wherein:
   (a) Ab is an antibody or a functional fragment thereof that specifically binds to mesothelin (MSLN);
   (b) L is a linker or does not exist;
   (c) D is a therapeutic agent; and
   (d) n is 1, 2, 3, 4, 5, 6, 7, or 8;
   wherein the antibody or the functional fragment thereof comprises a heavy chain variable region having an amino acid sequence that is at least 95% identical to SEQ ID NO: 7 and a light chain variable region having an amino acid sequence that is at least 95% identical to SEQ ID NO: 8, and wherein:
   (i) the heavy chain variable region comprises VH CDR1, VH CDR2, and VH CDR3 having an amino acid sequence as set forth in SEQ ID NO: 1, 2, and 3, respectively; and
   (ii) the light chain variable region comprises VL CDR1, VL CDR2, and VL CDR3 having an amino acid sequence as set forth in SEQ ID NO: 4, 5, and 6, respectively.

2. The antibody drug conjugate according to claim 1, wherein
   (i) the heavy chain variable region comprises an amino acid sequence as set forth in SEQ ID NO: 7; and
   (ii) the light chain variable region comprises an amino acid sequence as set forth in SEQ ID NO: 8.

3. The antibody drug conjugate according to claim 1, wherein the antibody is a monoclonal antibody, a chimeric antibody, a humanized antibody, a single chain antibody (scFv) or a bispecific antibody.

4. The antibody drug conjugate according to claim 1, wherein the therapeutic agent is a dolastatin peptide.

5. The antibody drug conjugate according to claim 1, wherein the linker and the antibody are linked by a thiol group on the antibody.

6. The antibody drug conjugate according to claim 1, wherein the linker has a structure as shown by the following formula:

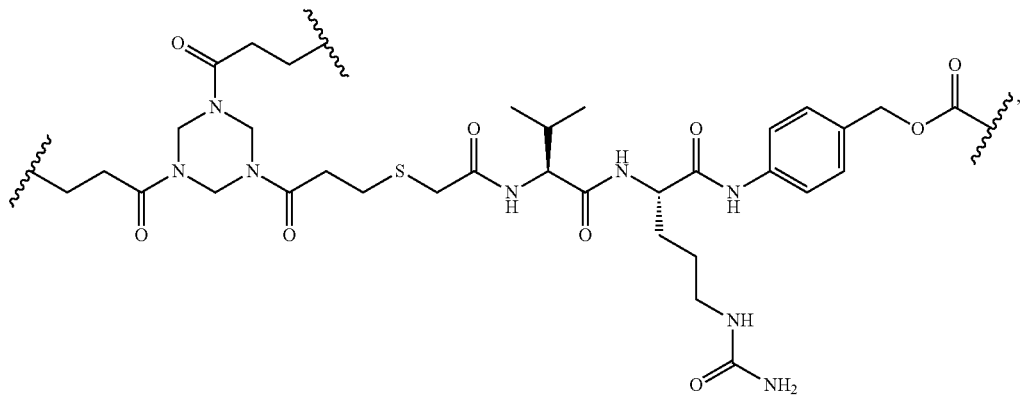 [SMILES: *CCC(=O)N1CN(C(=O)CC*)CN(C(=O)CCSCC(=O)N[C@H](C(=O)N[C@@H](CCCNC(N)=O)C(=O)Nc2ccc(COC(*)=O)cc2)C(C)C)C1]

or the linker has a structure as shown by the following formula:

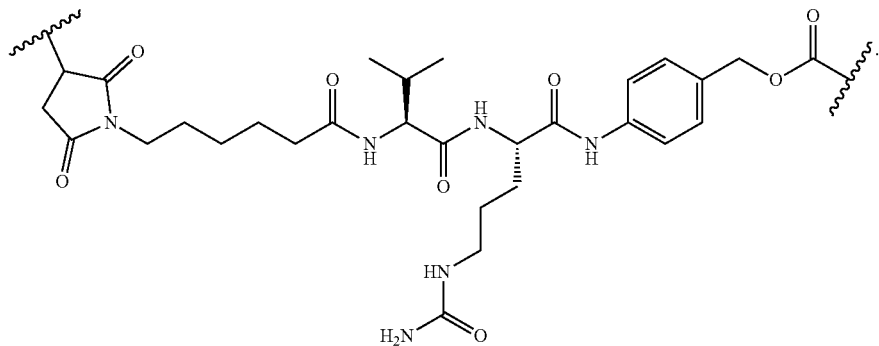 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

7. The antibody drug conjugate according to claim 1, which has a structure as shown in any one of the following formulas:

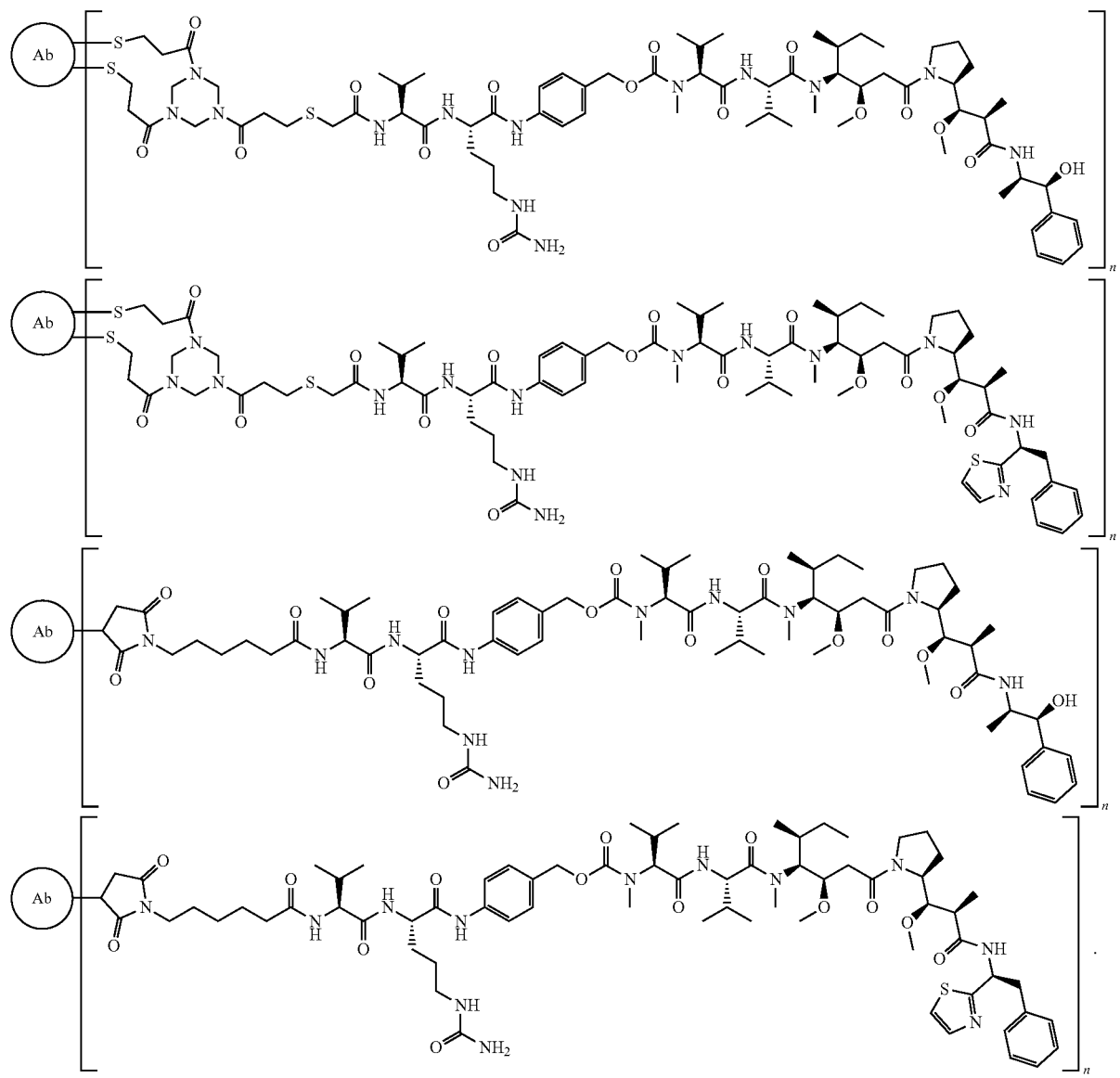

8. An antibody or a functional fragment thereof capable of specifically binding to mesothelin,
wherein the antibody or the functional fragment thereof comprises a heavy chain variable region having an amino acid sequence that is at least 95% identical to SEQ ID NO: 7 and a light chain variable region having an amino acid sequence that is at least 95% identical to SEQ ID NO: 8, and wherein:
(i) the heavy chain variable region comprises VH CDR1, VH CDR2, and VH CDR3 having an amino acid sequence as set forth in SEQ ID NO: 1, 2, and 3, respectively; and
(ii) the light chain variable region comprises VL CDR1, VL CDR2, and VL CDR3 having an amino acid sequence as set forth in SEQ ID NO: 4, 5, and 6, respectively.

9. The antibody or functional fragment thereof according to claim 8, wherein
(i) the heavy chain variable region comprises an amino acid sequence as set forth in SEQ ID NO: 7; and
(ii) the light chain variable region comprises an amino acid sequence as set forth in SEQ ID NO: 8.

10. The antibody or functional fragment thereof according to claim 8, wherein the antibody is a monoclonal antibody, a chimeric antibody, a humanized antibody, a single chain antibody (scFv) or a bispecific antibody.

11. An isolated polynucleotide, which encodes the antibody or functional fragment thereof according to claim 8.

12. An expression vector or a combination of expression vectors, which comprises the polynucleotide according to claim 11, the polynucleotide being operably linked to a regulatory sequence allowing the expression of a polypeptide encoded thereby in a host cell or a cell-free expression system.

13. A pharmaceutical composition, which comprises the conjugate according to claim 1, and a pharmaceutically acceptable carrier.

14. A method for treatment of a mesothelin-positive cancer, comprising administering a therapeutically effective amount of the conjugate according to claim 1 to a subject in need thereof.

15. A method for treatment of a mesothelin-positive cancer, comprising administering a therapeutically effective amount of the antibody or functional fragment thereof according to claim 8 to a subject in need thereof.

16. A method for treatment of a mesothelin-positive cancer, comprising administering a therapeutically effective amount of the polynucleotide according to claim 11 to a subject in need thereof.

17. A method for treatment of a mesothelin-positive cancer, comprising administering a therapeutically effective amount of the expression vector according to claim 12 to a subject in need thereof.

18. A method for treatment of a mesothelin-positive cancer, comprising administering a therapeutically effective amount of the pharmaceutical composition according to claim 13 to a subject in need thereof.

19. A pharmaceutical composition, which comprises the antibody or functional fragment thereof according to claim 8 and a pharmaceutically acceptable carrier.

20. The antibody drug conjugate according to claim 1, wherein the therapeutic agent is MMAD, MMAE or MMAF.

* * * * *